(12) United States Patent
Moore et al.

(10) Patent No.: US 11,242,374 B2
(45) Date of Patent: Feb. 8, 2022

(54) MINIMALLY-INVASIVE AND ACTIVITY-DEPENDENT CONTROL OF EXCITABLE CELLS

(71) Applicants: Brown University, Providence, RI (US); Central Michigan University, Mount Pleasant, MI (US)

(72) Inventors: Christopher I. Moore, Pawtucket, RI (US); Ute Hochgeschwender, Mount Pleasant, MI (US); Diane Lipscombe, Barrington, RI (US)

(73) Assignees: Brown University, Providence, RI (US); Central Michigan University, Mount Pleasant, MI (US)

( * ) Notice: Subject to any disclaimer, the term of this patent is extended or adjusted under 35 U.S.C. 154(b) by 513 days.

(21) Appl. No.: 15/545,428

(22) PCT Filed: Jan. 22, 2016

(86) PCT No.: PCT/US2016/014593
§ 371 (c)(1),
(2) Date: Jul. 21, 2017

(87) PCT Pub. No.: WO2016/118902
PCT Pub. Date: Jul. 28, 2016

(65) Prior Publication Data
US 2018/0044397 A1 Feb. 15, 2018

Related U.S. Application Data

(60) Provisional application No. 62/106,633, filed on Jan. 22, 2015.

(51) Int. Cl.
*C12N 5/0793* (2010.01)
*C07K 14/705* (2006.01)
*A61N 5/06* (2006.01)
*A01K 67/027* (2006.01)

(52) U.S. Cl.
CPC ........ *C07K 14/705* (2013.01); *A01K 67/0275* (2013.01); *A61N 5/062* (2013.01); *A01K 2217/052* (2013.01); *A01K 2217/206* (2013.01); *A01K 2227/105* (2013.01); *A01K 2267/0393* (2013.01); *C07K 2319/60* (2013.01); *C12N 2750/14141* (2013.01)

(58) Field of Classification Search
None
See application file for complete search history.

(56) References Cited

U.S. PATENT DOCUMENTS

| | | | |
|---|---|---|---|
| 5,677,158 A | 10/1997 | Zhou et al. | |
| 5,741,668 A | 4/1998 | Ward et al. | |
| 6,309,634 B1 | 10/2001 | Bankiewicz et al. | |
| 6,555,674 B2 | 4/2003 | Tornoe | |
| 6,683,058 B1 | 1/2004 | Tuszynski | |
| 9,687,672 B2 | 6/2017 | Brown et al. | |
| 2002/0037281 A1 | 3/2002 | Davidson et al. | |
| 2007/0141163 A1 | 6/2007 | Vitaliano et al. | |
| 2009/0088680 A1 | 4/2009 | Aravanis et al. | |
| 2011/0224752 A1 | 9/2011 | Rolston et al. | |
| 2011/0301529 A1 | 12/2011 | Zhang et al. | |
| 2012/0121542 A1 | 5/2012 | Chuong et al. | |
| 2013/0137113 A1 | 5/2013 | Isacoff et al. | |

FOREIGN PATENT DOCUMENTS

| | | |
|---|---|---|
| WO | 9524929 A2 | 9/1995 |
| WO | 9530761 A2 | 11/1995 |
| WO | WO-2009/019508 A1 | 2/2009 |
| WO | WO-2011/005978 A2 | 1/2011 |
| WO | WO-2012/054484 A1 | 4/2012 |
| WO | 2014028451 A1 | 2/2014 |

OTHER PUBLICATIONS

Emerich et al., "Central analgesic actions of loperamide following transient permeation of the blood brain barrier with Cereport (RMP-7)," 801(1-2):259-66 (1998).
International Search Report and Written Opinion for International Application No. PCT/US16/14593, dated Apr. 13, 2016 (18 pages).
Reinbothe et al., "Optogenetic control of insulin secretion in intact pancreatic islets with beta-cell-specific expression of Channelrhodopsin-2," Islets. 6(1):e28095 (2014) (8 pages).
Benoist et al., "In Vivo Sequence Requirements of the SV40 Early Promoter Region", Nature, vol. 290, Mar. 26, 1981, pp. 304-310.
Berglund et al., Combined optogenetic and chemogenetic control of neurons, Methods Mol. Biol., 1408, 207-225 (2016).
Berglund et al., Light-emitting channelrhodopsins for combined optogenetic and chemical-genetic control of neurons, PLoS One, 8(3), e59759 (2013).
Chen et al.. Dysfunction of cortical GABAergic neurons leads to sensory hyper-reactivity in a Shank3 mouse model of ASD, Nature Neurosci., 23(4), (2020).
Chiken & Nambu, Mechanism of deep brain stimulation: Inhibition, excitation, or disruption? The Neuroscientist, 22(3) 313-322 (2016).
Chopek et al., Multistable properties of human subthalamic nucleus neurons in Parkinson's disease, Proc. Natl. Acad. Sc., U.S.A., 116(48), 24326-24333 (Nov. 2019).
(Continued)

*Primary Examiner* — Michael D Pak
(74) *Attorney, Agent, or Firm* — Adler Pollock & Sheehan P.C.

(57) ABSTRACT

The present invention provides a method of bioluminescence-driven optogenetic control of excitable cells. The excitable cell expresses a light-gated ion channel, and a luminescent protein can be expressed either in the excitable cell or in another cell proximal to the excitable cell. The methods of the invention can be used to desynchronize local activity of excitable cells in a mammalian tissue. The methods of the invention can be used to treat a disease or condition in a mammal, the disease or condition being related to bursting. The disease or condition can be Parkinson's disease, epilepsy, a sleep disorder, or a sensory-related disease or condition (e.g., attention deficit disorder or pain). The invention also provides a conjugate of containing a voltage-gated ion channel and a luminescent protein.

20 Claims, 12 Drawing Sheets

Specification includes a Sequence Listing.

(56) References Cited

OTHER PUBLICATIONS

Cowan et al., "Targeting Gene Expression to Endothelial Cells in Transgenic Mice Using the Human Intercellular Adhesion Molecule 2 Promoter", Transplantation, vol. 62, Issue 2, Jul. 27, 1996, pp. 155-160.

Dayal et al., Subthalamic nucleus deep brain stimulation in Parkinson's disease: The effect of varying stimulation parameters, J. Parkinson's Dis., 7, 235-245 (2017).

Dumont et al., "Tek, A Novel Tyrosine Kinase Gene Located on Mouse Chromosome 4, is Expressed in Endothelial Cells and Their Presumptive Precursors", Oncogene, vol. 7, No. 8, Aug. 1992, pp. 1471-1480.

Fromm et al., "Deletion Mapping of DNA Regions Required for SV40 Early Region Promoter Function in Vivo", J. Mol. Appl. Genet., vol. 1, No. 5, 1982, pp. 457-481.

Gomez-Ramirez et al., The BioLuminescent-OptoGenetic in vivo response to coelenterazine is proportional, sensitive and specific in neocortex, bioRxiv (Jul. 22, 2019).

Gradinaru et al., "eNpHR: A Natronomonas Halorhodopsin Enhanced for Optogenetic Applications", Brain Cell Biol., vol. 36, No. 1-4, Aug. 2008, pp. 129-139.

Gradinaru et al., "Molecular and Cellular Approaches for Diversifying and Extending Optogenetics", Cell, vol. 141, No. 1, Apr. 2, 2010, pp. 154-165.

Gruss et al., "Simian Virus 40 Tandem Repeated Sequences as an Element of the Early Promoter", Proc. Natl. Acad. Sci., vol. 78, No. 2, Feb. 1981, pp. 943-947.

Hamani et al., Subthalamic nucleus deep brain stimulation: Basic concepts and novel perspectives. eNeuro, 4(5), e0140-17 (2017).

Helton et al., "Neuronal L-Type Calcium Channels Open Quickly and are Inhibited Slowly", J. Neurosci., vol. 25, No. 44, Nov. 2, 2005, p. 10247-10251.

Hisatsune et al., "High Level of Endothelial Cell-Specific Gene Expression by a Combination of the 5? Flanking Region and the 5? Half of the First Intron of the VE-Cadherin Gene", Blood, vol. 105, 2005, pp. 4657-4663.

Lassalle et al., "ESM-1 Is a Novel Human Endothelial Cell-Specific Molecule Expressed in Lung and Regulated by Cytokines", Journal of Biological Chemistry, vol. 271, No. 34, Aug. 1996, p. 20458-20464.

Levy et al., High-frequency synchronization of neuronal activity in the subthalamic nucleus of Parkinsonian patients with limb tremor, J. Neurosci., 20(20), 7766-7775 (Oct. 15, 2000).

Moreau et al., "The SV40 72 Base Repair Repeat has a Striking Effect on Gene Expression Both in SV40 and Other Chimeric Recombinants", Nucleic Acids Res., vol. 9, No. 22, Nov. 25, 1981, pp. 6047-6068.

Nicklin et al., "Analysis of Cell-Specific Promoters for Viral Gene Therapy Targeted at the Vascular Endothelium", Hypertension., vol. 38, No. 1, Jul. 2001, pp. 65-70.

Pan et al., "Alternative Splicing in the Cytoplasmic II-III Loop of the N-type Ca Channel Alpha 1B Subunit: Functional Differences are Beta Subunit-Specific", J. Neurosci., vol. 20, No. 13, 2000, pp. 4769-4775.

Park et al., Fine temporal structure of beta oscillations synchronization in subthalamic nucleus in Parkinson's disease, J. Neurophysiol., 103(5), 2707-2716 (2010).

Paz et al. Closed-loop optogenetic control of thalamus as a tool for interrupting seizures after cortical injury. Nature Neuroscience, 16(1), 64-70 (Jan. 2013).

Ramirez-Zamora & Ostrem, Globus pallidus interna or subthalamic nucleus deep brain stimulation for Parkinson disease: A review, JAMA Neurology, 75(3), 367-372 (Mar. 2018).

Schnurch et al., "Expression of Tie-2, A Member of a Novel Family of Receptor Tyrosine Kinases, in the Endothelial Cell Lineage", Development, vol. 119, No. 3, Nov. 1, 1993, pp. 957-968.

Xu et al., "Neuronal Ca(V)1.3alpha(1) L-Type Channels Activate at Relatively Hyperpolarized Membrane Potentials and are Incompletely Inhibited by Dihydropyridines", J. Neurosci., vol. 21, No. 16, Aug. 15, 2001, pp. 5944-5951.

Zhang et al., "Multimodal Fast Optical Interrogation of Neural Circuitry", Nature, vol. 446, No. 7136, Apr. 5, 2007, pp. 633-639.

SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct

<400> SEQUENCE: 1

Glu Ser Asp Val
1

```
<210> SEQ ID NO 2
<211> LENGTH: 12
<212> TYPE: PRT
<213> ORGANISM: Artificial Sequence
<220> FEATURE:
<223> OTHER INFORMATION: Synthetic Construct

<400> SEQUENCE: 2

Ile Tyr His Lys Val Lys Arg Val Ile Glu Asp Leu
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Synthetic Construct

<400> SEQUENCE: 3

Gly Asp Pro Leu Val Gln Cys Gly Gly Ile Ala Gly Ser Ala Thr
1               5                   10                  15

<210> SEQ ID NO 4
<211> LENGTH: 50
<212> TYPE: PRT
<213> ORGANISM: Artificial Sequence
<220> FEATURE:
<223> OTHER INFORMATION: Synthetic Construct

<400> SEQUENCE: 4

Ser Gly Gly Ser Gly Ser Gly Gly Gln Ser Gly Gly Ser Gly Ser Gly
1               5                   10                  15

Gly Gln Ser Gly Gly Ser Gly Ser Gly Gly Gln Ser Gly Gly Ser Gly
                20                  25                  30

Ser Gly Gly Gln Ser Gly Gly Ser Gly Ser Gly Gly Gln Ser Gly Leu
        35                  40                  45

Arg Ser
    50
```

MINIMALLY-INVASIVE AND ACTIVITY-DEPENDENT CONTROL OF EXCITABLE CELLS

CROSS-REFERENCE TO RELATED APPLICATIONS

The present application is a National Stage Entry of PCT/US2016/014593 filed Jan. 22, 2016 and claims benefit of U.S. Provisional Patent Application No. 62/106,633 filed Jan. 22, 2015, the entire contents of which are incorporated herein by reference.

FIELD OF THE INVENTION

The present invention relates to a minimally-invasive modulation of the activity of an excitable cell using bioluminescence-driven optogenetic methods.

BACKGROUND

Polarization of excitable cells (e.g., neurons) plays a role in symptoms of various diseases or conditions (e.g., Parkinson's disease, epilepsy, sleep and sensory-related maladies such as pain and attention deficit disorders). While etiologies of these diseases or conditions may differ, their manifestation can involve the same basic processes, such as hyperpolarization of excitable cells. For example, increases in bursting (brief periods of high-frequency action potential activity) are prominent in epilepsy and Parkinson's disease. Epileptic seizures are believed to be driven by hypersynchronized bursting in the thalamic reticular nucleus (TRN) and in thalamic relay neurons that project to the neocortex. In Parkinson's disease patients, bursting occurs in subthalamic nucleus and increases after dopamine depletion.

Modulation of polarization of excitable cells has been the focus of many studies in the field of optogenetics. Existing optogenetic approaches typically up- or down-regulate activity of cells in a tissue en masse and thus can up- or down-regulate the activity of cells that are not in need thereof. Moreover, delivery of light often requires the use of chronic implanted devices, which may be fully or partially implanted. If automatic control of optogenetic control is desired in a device, additional elements, such as implanted electrodes, may be required, rendering such approaches invasive.

There remains a need for minimally invasive methods of optogenetic control, preferably automatic control that requires little input from patient or medical personnel. The methods capable of providing targeted optogenetic control are particularly desirable. The present invention can provide optogenetic control with the desirable characteristics described herein.

SUMMARY OF THE INVENTION

In general, the present invention relates to a bioluminescence-driven optogenetic approach to modulating an activity of an excitable cell (e.g., in a mammalian tissue). Modulation of the activity can provide in various aspects and embodiments: desynchronization of activity of a population of excitable cells in a mammalian tissue; control of bursting activity in excitable cells; and treatment for a disease or a condition associated with bursting in excitable cells.

The present invention provides the following methods:

A Method of Modulating Activity of an Excitable Cell Expressing a Luminescent Protein and a Conjugate of a Light-Gated Ion Channel and a Subcellular Element in a Tissue in a Mammal.

The method can involve contacting a luciferin with the cell, where the luciferin undergoes an oxidation reaction mediated by the luminescent protein to produce light, thereby modulating the activity of the excitable cell. The subcellular element can be, e.g., a voltage-gated ion channel.

A Method of Modulating Activity of an Excitable Cell Expressing a Light-Gated Ion Channel and a Luminescent Protein in a Tissue in a Mammal.

The method can involve contacting a luciferin with the cell; the luciferin undergoes an oxidation reaction mediated by the luminescent protein to produce light, thereby modulating activity of the excitable cell.

A Method of Desynchronizing the Activity of Excitable Cells in a Tissue.

The method can involve contacting the tissue with a luciferin, provided that the tissue contains excitable cells heterogeneously expressing a light-gated ion channel and a luminescent protein, and where the luciferin reacts with the luminescent protein to produce light, thereby modulating the activity of the light-gated ion channel and desynchronizing the activity of the excitable cells in the tissue. Alternatively, the method can involve contacting the tissue with a luciferin, provided that the excitable cell expresses a light-gated ion channel and a luminescent protein, and the luciferin can undergo an oxidation reaction mediated by the luminescent protein to produce light, thereby altering activity of the light-gated ion channel and desynchronizing activity of the excitable cell.

A Method of Desynchronizing a Population of Excitable Cells in a Tissue.

The method can involve contacting the tissue with a luciferin, provided that at least one of the excitable cells expresses a light-gated ion channel and a luminescent protein, and the luciferin can react with the luminescent protein to produce light, thereby altering activity of the light-gated ion channel and desynchronizing activity of the population of excitable cells. Alternatively, the method can involve expressing a light-gated ion channel in a first population of excitable cells in the tissue, expressing a luminescent protein in a second population of excitable cells in the tissue, and contacting the tissue with a luciferin, where the luciferin reacts with the luminescent protein to produce light, thereby modulating the activity of the light-gated ion channel and desynchronizing the activity of excitable cells in the tissue.

A Method of Treating a Disease or Condition in a Mammal.

The disease or condition can, e.g., be associated with bursting. The method can involve contacting an affected tissue in the mammal with a luciferin, provided that the tissue contains an excitable cell expressing a light-gated ion channel and a luminescent protein, and the luciferin can undergo an oxidation reaction mediated by the luminescent protein to produce light, thereby altering activity of the light-gated ion channel and treating the disease or condition. Alternatively, the method can involve contacting an affected tissue in the mammal with a luciferin, wherein the tissue contains excitable cells heterogeneously expressing a light-gated ion channel and a luminescent protein, and the luciferin undergoes an oxidation reaction mediated by the luminescent protein to produce light, thereby modulating the activity of the light-gated ion channel and treating the disease or condition. Alternatively, the method can involve contacting an affected tissue in the mammal with a luciferin, the tissue containing (i) an excitable cell expressing a light-gated ion channel and (ii) a cell expressing a conjugate containing a luminescent protein and a voltage-gated ion channel and being proximal to the excitable cell, where the luciferin undergoes an oxidation reaction mediated by the luminescent protein to produce light, thereby modulating the activity of the light-gated ion channel and treating the disease or condition.

A Method of Modulating Activity of an Excitable Cell Expressing a Light-Gated Ion Channel in a Tissue in a Mammal.

The method can involve contacting a luciferin with a cell expressing a luminescent protein and being proximal to the excitable cell; the luciferin can undergo an oxidation reaction mediated by the luminescent protein to produce light, thereby modulating activity of the excitable cell.

A Method of Desynchronizing Local Activity of an Excitable Cell (e.g., Driven by Calcium Increases in a Tissue).

The method can involve contacting the tissue with a luciferin, the tissue containing the excitable cell and a cell expressing a luminescent protein proximal to the excitable cell, the excitable cell expressing a light-gated ion channel; the luciferin can undergo an oxidation reaction mediated by with the luminescent protein to produce light, thereby altering activity of the light-gated ion channel and desynchronizing activity of the excitable cell. Alternatively, the method can involve contacting the tissue with a luciferin, the tissue containing the excitable cell and a cell expressing a conjugate including a luminescent protein and a voltage-gated ion channel proximal to the excitable cell, the excitable cell expressing a light-gated ion channel, where the luciferin undergoes an oxidation reaction mediated by with the luminescent protein to produce light, thereby modulating the activity of the light-gated ion channel and desynchronizing activity of the excitable cell.

A Method of Treating a Disease or Condition in a Mammal.

The disease or condition is associated with bursting. The method can involve contacting an affected tissue in the mammal with a luciferin, the tissue containing (i) an excitable cell expressing a light-gated ion channel and (ii) a cell expressing a luminescent protein and being proximal to the excitable cell; the luciferin can undergo an oxidation reaction mediated by the luminescent protein to produce light, thereby altering activity of the light-gated ion channel and treating the disease or condition.

A Method of Desynchronizing a Population of Excitable Cells in a Tissue.

The method can involve contacting the tissue with a luciferin, at least one the excitable cell expressing a light-gated ion channel, and the tissue containing a cell expressing a luminescent protein. The luciferin can undergo an oxidation reaction mediated by the luminescent protein to produce light, thereby altering/modulating the activity of the light-gated ion channel and desynchronizing activity of the population of excitable cells. Alternatively, the method can involve contacting the tissue with a luciferin, at least one the excitable cell expressing a light-gated ion channel, and the tissue containing a cell expressing a conjugate containing a luminescent protein and a voltage-gated ion channel, where the luciferin undergoes an oxidation reaction mediated by the luminescent protein to produce light, thereby modulating the activity of the light-gated ion channel and desynchronizing activity of the population of excitable cells.

In any of the above methods, the excitable cell can be, e.g., a neuron, a muscle cell, or an endocrine cell (e.g., a pituitary cell, a β-cell in an islet of Langerhans, or a cell in adrenal medulla). The excitable cell can be a neuron. The tissue can be subthalamic nucleus or thalamic reticular nucleus.

Synchronization of excitable cells in the tissue can be associated with a disease or condition. The disease or condition can be, e.g., Parkinson's disease, epilepsy, a sleep disorder, or a sensory-related disorder or condition (e.g., pain or attention-deficit disorder).

In the above methods featuring plurality of excitable cells (e.g., a population of excitable cells), the tissue may contain excitable cells, e.g., expressing a second luminescent protein and a second light-gated ion channel, where the luciferin undergoes an oxidation reaction mediated by the second luminescent protein to produce light, thereby modulating the activity of the second light-gated ion channel and enhancing the treating of the disease or condition. In some embodiments of these methods, the excitable cells heterogeneously express the second luminescent protein and the second light-gated ion channel.

The luminescent protein can be conjugated to the light-gated ion channel. In some embodiments, the luminescent protein is a fusion protein. Alternatively, the luminescent protein can be conjugated to a voltage-gated ion channel (e.g., a Cav channel (e.g., Cav1.2, Cav2.1, or Cav3.3)). Luminescence of the luminescent protein can, e.g., be dependent on concentration of ions (e.g., $Ca^{2+}$ ions). In some embodiments, the luminescent protein contains a luciferase (e.g., a *Gaussia* luciferase). In some embodiments, the luminescent protein contains a photoprotein (e.g., an Aequorin). In some embodiments, the luminescent protein contains a fluorescent protein (e.g., a Green Fluorescent Protein, a Red Fluorescent Protein, or a Yellow Fluorescent Protein). In some embodiments, the luminescent protein contains a calmodulin domain or a $Ca^{2+}$-binding domain thereof. In some embodiments, the luminescent protein can be conjugated to a targeting moiety. In some embodiments, the targeting moiety can be targeting dendritic postsynaptic density.

In some embodiments, the light-gated ion channel is ChR1, ChR2, VChR1, ChR2 C128A, ChR2 C128S, ChR2 C128T, ReaChR, C1V1, iC1C2, ChD, ChEF, ChF, ChIEF, NpHR, eNpHR, Halo, Arch 3.0, Arch T 3.0, Mac 3.0, or melanopsin, or a chimera of these proteins or a natural or an engineered variant thereof. In certain embodiments, the light-gated ion channel is ChR2 or VChR1.

The luciferin can be, e.g., a coelenterazine.

The methods of the invention can further involve, prior to the contacting with the luciferin, expressing the luminescent protein in the tissue. Expressing the luminescent protein can involve introducing a recombinant nucleic acid encoding the luminescent protein into the tissue or a precursor thereof.

The methods of the invention can further involve, prior to the contacting with the luciferin, expressing the light-gated ion channel in the tissue. Expressing the light-gated ion-channel can involve introducing a recombinant nucleic acid encoding the light-gated ion channel into the tissue or a precursor thereof.

In the methods of the invention, the contacting the luciferin can involve expressing the luciferin in a cell in the tissue. Expressing the luciferin can involve introducing a recombinant nucleic acid encoding a precursor for biosynthesis of the luciferin into the tissue or a precursor thereof.

Introducing recombinant nucleic acid can involve transducing or transfecting the recombinant nucleic acid into the cell or a precursor thereof. In some embodiments, the recombinant nucleic acid is encapsidated within a recombinant virus selected from the group consisting of recombinant adeno-associated virus (AAV), recombinant retrovirus, recombinant lentivirus, recombinant poxvirus, recombinant rabies virus, recombinant pseudo-rabies virus, recombinant herpes simplex virus, and human immunodeficiency virus (HIV). In some embodiments, the virus is administered to the mammal parenterally (e.g., by an intravenous injection, an intraarterial injection, an intrathecal injection, an intracranial injection, or an intramuscular injection).

The invention also provides a conjugate containing a voltage-gated ion channel (e.g., a Cav channel (e.g., Cav1.2, Cav2.1, or Cav3.3)) and a luminescent protein. In some embodiments, luminescence of the luminescent protein can be dependent on concentration of ions (e.g., $Ca^{2+}$ ions). In some embodiments, the luminescent protein contains a luciferase (e.g., a *Gaussia* luciferase). In some embodiments, the luminescent protein contains a photoprotein (e.g., an Aequorin). In some embodiments, the luminescent protein is conjugated at C-terminus of the voltage-gated ion channel. In some embodiments, the conjugate further includes a targeting moiety (e.g., the moiety targeting dendritic postsynaptic density). In some embodiments, the conjugate is a fusion protein.

The invention provides a nucleic acid encoding the conjugate of the invention, as described herein. The invention also provides a pharmaceutical composition containing the nucleic acid of the invention, as described herein. In the pharmaceutical composition of the invention, the nucleic acid may be encapsidated in a virus.

The invention also provides an excitable cell expressing the conjugate of the invention, as described herein.

DEFINITIONS

The term "expressing a luminescent protein," as used herein, refers to the production of one or more exogenous luminescent proteins that impact cell physiology (e.g., molecular channel proteins) in a cell into which a recombinant nucleic acid molecule encoding the light-activated molecular channel protein has been introduced.

The term "light-gated ion channel," as used herein, refers to an ion-gated membrane channel protein that is activated by absorbing electromagnetic radiation. A light-gated ion channel can be, e.g., a luminescence-activated $Ca^{2+}$ channel, a luminescence-activated $Na^+$ channel, a luminescence-activated $K^+$ channel, a luminescence-activated $Cl^-$ channel, or a luminescence-activated proton pump. Non-limiting examples of light-gated ion channels include ChR1, ChR2, VChR1, ChR2 C128A, ChR2 C128S, ChR2 C128T, ReaChR, C1V1, C1V1 E122T, iC1C2, ChD, ChEF, ChF, ChIEF, NpHR, eNpHR, Halo, Arch 3.0, Arch T 3.0, Mac 3.0, and melanopsin. Light-gated ion channels can be wild-type or mutant, e.g., red-shifted (e.g., ReaChR, C1V1, C1V1 E122T, or Halo or a modification thereof (e.g., those described in US 2012/0121542; the light-activated ion pumps of which are incorporated herein by reference)).

The term "luminescent protein," as used herein, refers to a protein capable of converting chemical energy into electromagnetic radiation through an oxidation reaction. Luciferin is a substrate for the oxidation reaction. A luminescent protein can be, e.g., a luciferase (e.g., *Gaussia* luciferase) or a photoprotein (e.g., Aequorin and Obelin). Luciferases catalyze oxidation of a luciferin (e.g., coelenterazine) and produce light as a byproduct of this reaction. A photoprotein coordinates to a luciferin and to molecular oxygen, and the oxidation reaction is then triggered by a stimulus (e.g., by $Ca^{2+}$ ions). A luminescent protein can be, e.g., wild-type or mutant, e.g., modified to enhance luminescence or modified to enhance. Non-limiting examples of mutant luminescent proteins include GLuc M43I, GLuc Y97W, GLuc I90L, Monsta (GLuc having F89W, I90L, H95E, and Y97W mutations), and GLuc4 (L30S, L40P, M43V).

The term "proximal," as used herein, refers to a cell expressing a light-gated ion channel, the cell being located within the photon transmission distance of a luminescent protein in another cell. The photons emitted by the luminescent protein are capable of reaching and activating the light-gated ion channel expressed the proximal cell.

The term "targeting moiety," as used herein, refers to a polypeptide exhibiting affinity for a specific subcellular compartment or element. Thus, incorporating a targeting moiety in a molecule allows for the molecule to be preferentially delivered to the specific subcellular compartment or element. Non-limiting examples of targeting moieties include dendritic localization motifs, e.g., polypeptide ESDV and IYHKVKRVIEDL.

As used herein, "treatment" is an approach for obtaining beneficial or desired results, e.g., clinical results. Beneficial or desired results include diminishment of extent of or palliation of the disease, disorder, or condition. "Palliating" a disease, disorder, or condition means that the extent and/or undesirable clinical manifestations of the disease, disorder, or condition are lessened and/or time course of the symptoms is shortened, as compared to the extent or time course in the absence of treatment.

The term "heterogeneously," when used herein in reference to the expression of two different proteins in cells, refers to a preferred expression of one of the two different proteins in one cell and of the other of the two different proteins in another cell with cells expressing both of the two different proteins being disfavored.

BRIEF DESCRIPTION OF THE DRAWINGS

FIG. 12A is a schematic of the multi electrode array. FIGS. 12B and 12C are images of the electrode array. The standard electrode layout grid of 8×8 is shown in FIG. 12B. FIG. 12D is a fluorescent image of MEA culture of rat cortical neurons transduced with AAV-hSyn-LMO3, where LMO3 is a fusion of sbGLuc and VChR1. Neurons are visible in fluorescent green, because of the expression of LMO3, which includes EYFP.

DETAILED DESCRIPTION

The present invention provides a non-invasive method of modulating activity (e.g., depolarization) of an excitable cell in a mammal (e.g., a human). The invention takes advantage of bioluminescence to drive optogenetic responses. Thus, the method of invention can eliminate the need for fully or partially implanted devices to detect the activity (e.g., hyperpolarization) of an excitable cell in a mammal (e.g., a human) and to deliver light to the excitable cell. According to the methods of the invention, bioluminescence activation can take place in response to a cellular condition (e.g., in response to cell membrane hyperpolarization). Thus, the methods of the invention can be used for targeted modulation of the activity of an excitable cell (e.g., a neuron).

Figure 1A:
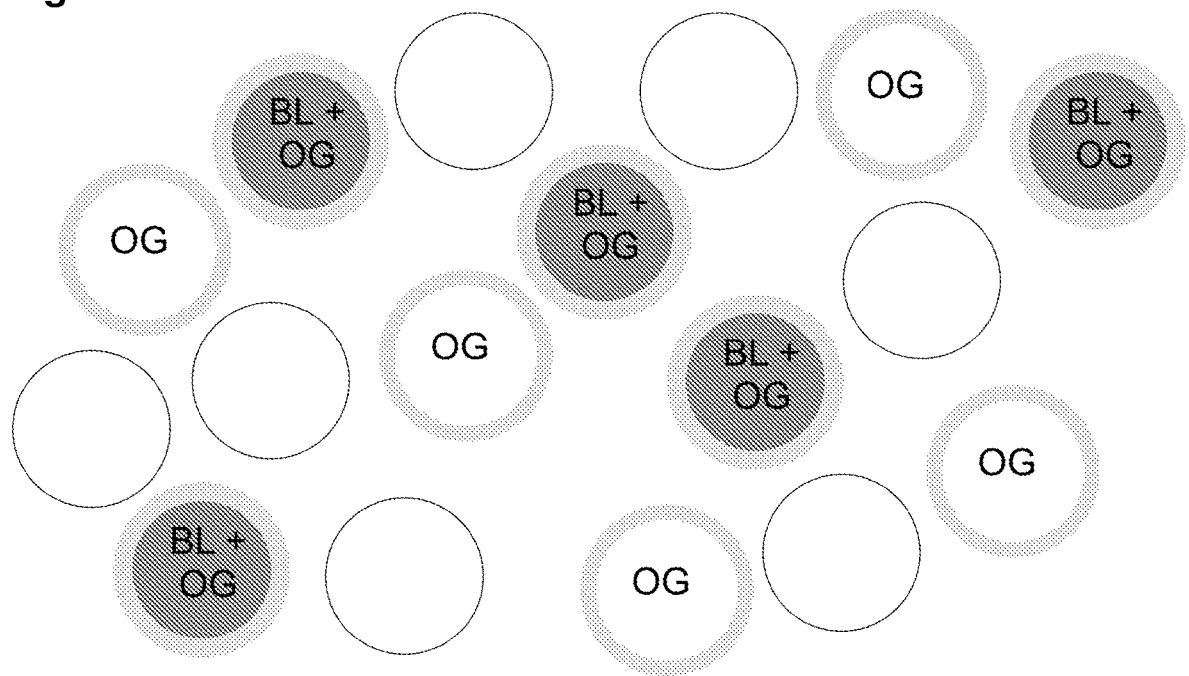
FIG. 1A is a scheme showing a population of excitable cells, some of which are expressing optogenetic (identified as OG in FIG. 1A) reagents (e.g., a light-gated ion channel) only, while others are expressing bioluminescent/optogenetic (identified as BL+OG in FIG. 1A) reagents (e.g., a luminescent protein and a light-gated ion channel, which may be expressed as a fusion protein or as two separate proteins).
Figure 1B:
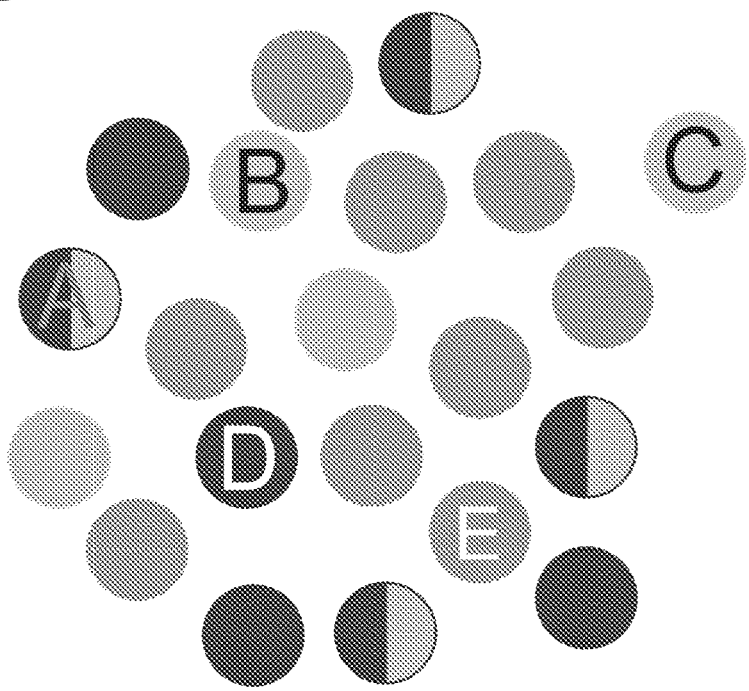
FIG. 1B is a scheme showing excitable cells including a population of excitable cells expressing a luminescent protein and a light-gated ion channel (labeled A), a population of excitable cells expressing a light-gated ion channel (labeled B and C), a population of excitable cells expressing a luminescent protein (labeled D), and a population of excitable cells not expressing a luminescent protein or a light-gated ion channel (labeled E). The shortest distance between the cell labeled B and the closest to B cell expressing a luminescent protein is smaller than that between the cell labeled C and the closes to C cell expressing a luminescent protein.
Figure 1C:
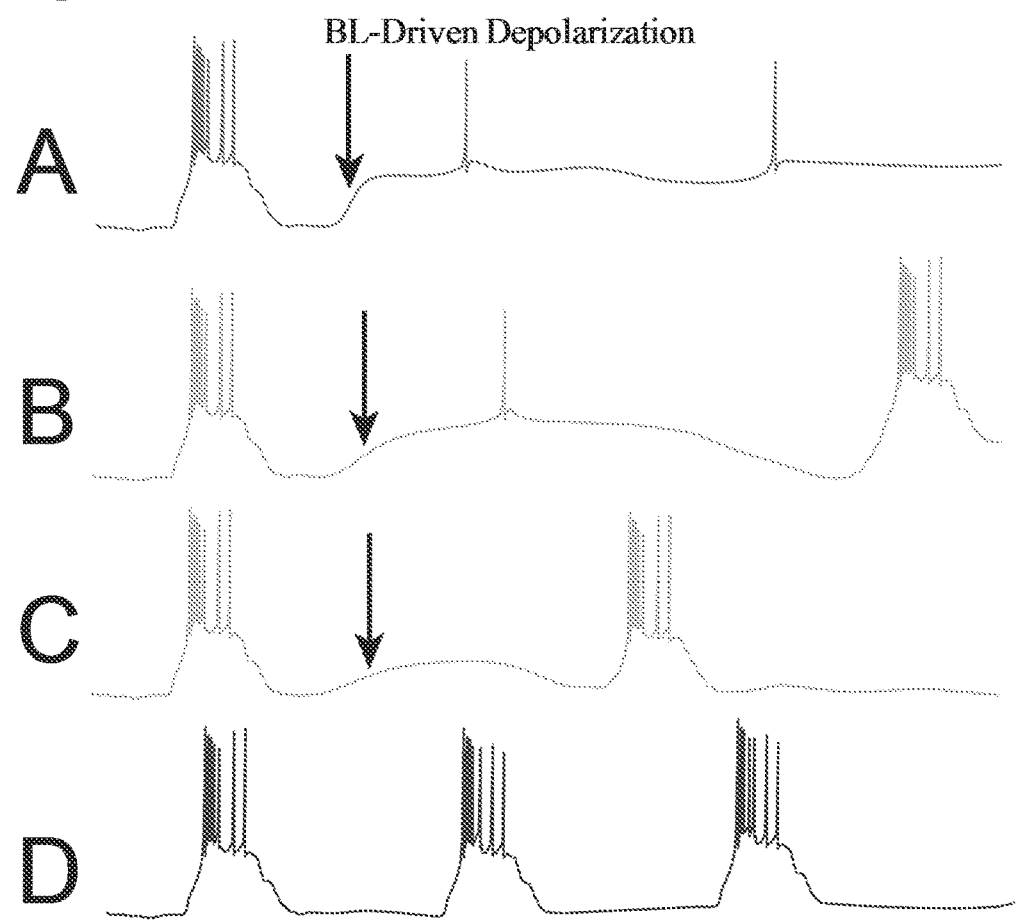
FIG. 1C is a series of graphs showing membrane potentials for the populations of excitable cells identified in FIG. 1B. The graphs labeled A, B, C, and D show membrane potentials for the populations of cells labeled A, B, C, and D, respectively, in FIG. 1B.

The present invention provides methods and tools for modulating activity of an excitable cell in a mammalian tissue (e.g., modulating a population of excitable cells, e.g., for controlling bursts or for desynchronizing an otherwise homogeneous population of excitable cells (e.g., neurons)). Modulation of the activity of a population of excitable cells in a tissue may be achieved by expressing a light-gated ion channel in a subpopulation of cells and by expressing a luminescent protein in the same, a different, or an overlapping subpopulation of excitable cells. The population of excitable cells in the tissue thus can become self-regulating. In a first approach, the subpopulation of excitable cells expressing a light-gated ion channel is the same as, or substantially overlapping with, the subpopulation of cells expressing a luminescent protein. In this approach, modulation of the activity of excitable cells in the tissue (e.g., desynchronization) can be rapid and powerful upon exposure to a luciferin. In a second approach, the subpopulation of excitable cells expressing a light-gated ion channel minimally overlaps or does not overlap with the subpopulation of cells expressing a luminescent protein. In this approach, modulation of the activity of excitable cells in the tissue (e.g., desynchronization) can be weaker and effectively slower than that described in the first approach upon exposure to a luciferin. The overlap between the two subpopulations of cells and the extent of the expression of each of a light-gated ion channel and a luminescent protein can be determined for each patient population, e.g., by standard titration of viruses prior to their administration (e.g., parenteral administration). Non-limiting examples of the approaches described herein are provided in FIGS. 1A and 1B.

The luminescent protein can be ion-sensitive (e.g., a photoprotein or a $Ca^{2+}$-sensitive luciferase) or persistent (i.e., not requiring external stimuli other than the presence of a luciferin, oxygen, and optionally an energy molecule, such as ATP, or a reducing molecule, such as flavin mononucleotide ($FMNH_2$)). Some or all of the luminescent protein can be conjugated to a targeting moiety. Also, some or all of the luminescent proteins can be provided in a single conjugate with a light-gated ion channel (e.g., a fusion protein). Alternatively, some or all of the luminescent proteins can be conjugated to a voltage-gated ion channel. Without being bound by a theory, light emitted by the luminescent protein-mediated oxidation of the luciferin can be captured by the light-gated ion channel in the same or different cell, which can lead to influx or efflux of the ions specific to the light-gated ion channel. Without being bound by a theory, the bioluminescence from the luminescent protein-mediated oxidation of the luciferin can activate the light-gated ion channel for influx or efflux of the ions (e.g., $Ca^{2+}$, $K^+$, $Na^+$, $H^+$, or $Cl^-$), thereby hyperpolarizing or depolarizing the cell having the light-gated ion channel. For example, influx of cations (e.g., $Ca^{2+}$, $K^+$, or $Na^+$) can cause depolarization of the cell, whereas efflux of cations can cause hyperpolarization of the cell. Thus, the modulation of the activity of a subpopulation of excitable cells in a tissue (e.g., hyperpolarization, depolarization, or hyperpolarization of one subset of excitable cells and depolarization of another subset of excitable cells) can control bursting in excitable cells (e.g., in neurons) and/or lead to desynchronization of the activity of a population of excitable cells in a tissue.

The invention also features the tools that can be used in the methods of the invention. For example, the invention provides a conjugate containing a voltage-gated ion channel (e.g., a Cav channel) and a luminescent protein (e.g., a $Ca^{2+}$-sensitive luciferase or a photoprotein (e.g., Aequorin)).

Excitable Cells and Modulation of their Activity

Excitable cells are known in the art; they are capable of producing and responding to electric cells. Non-limiting examples of excitable cells include neurons, muscle cells, heart cells, and endocrine cells (e.g., pituitary cells, β-cells in islets of Langerhans, and cells in adrenal medulla). Cell membranes of all cells in mammals are polarized because of the difference between extracellular and intracellular concentrations of cations and anions. This difference in concentrations is maintained by ion pumps (e.g., sodium-potassium pumps or proton pumps). Hyperpolarization of a cell is a change in polarization in a cell membrane potential due to the increase in the net concentration of negative charges (anions) inside the cell relatively to the net concentration of negative charges outside the cell. Hyperpolarization can be achieved through influx of anions and efflux of cations. Depolarization is opposite to hyperpolarization and involves the decrease in net concentration of negative charges inside the cell relatively to the net concentration of negative charges outside the cell.

Modulation of the activity of excitable cells (e.g., desynchronization of the activity of a population of excitable cells and/or control of bursting in excitable cells) can be used to treat various diseases or conditions associated with abnormal patterns of activity of the excitable cells, e.g., bursting. For example, increases in bursting (brief periods of high-frequency action potential activity) are prominent in epilepsy and Parkinson's disease. Epileptic seizures are believed to be driven by hyper-synchronized bursting in the thalamic reticular nucleus (TRN) and in thalamic relay neurons that project to the neocortex. In Parkinson's disease patients, bursting occurs in subthalamic nucleus and increases after dopamine depletion. Thus, by targeting certain excitable cells, a variety of diseases or conditions can be treated (e.g., palliated). The disease or condition can be Parkinson's disease, epilepsy, a sleep disorder, attention deficit disorder, or pain.

Attention deficit disorder (ADD) is typically considered a disease driven by inability to control selective attention. Children and adults with ADD cannot maintain focus on topic, goals, or projects for sustained periods of time, ostensibly because they are unable to devalue inputs dynamically from other distracters in their environment. The ability to sustain focus through sustained activation in relevant neurons specifically, or through increased activity in the neuromodulatory systems driving neural activity, may be key to effective treatment of ADD. Dendritic calcium spikes are believed to be crucial for amplifying perceptual signals. The present invention can provide a robust and minimally invasive approach to specific upregulation of the circuits of interest. Thus, the present invention can provide a minimally invasive approach to the treatment of attention deficit disorder.

Dendritic calcium spikes (e.g., in the neocortex and hippocampus) and astrocytic calcium are believed to be crucial for plasticity. Thus, the present invention can provide a minimally invasive approach to the treatment of diseases of learning or of plasticity (e.g., Alzheimer's Disease).

Pain disorders have recently been characterized as altered bursting in the relay thalamic nuclei associated with expression of alpha oscillations recorded in neocortex. Bursting in thalamus can be a driver of the pain percept, and transitioning these neurons from a burst to a tonic firing mode can therefore be used to treat the focus of pain origin. Alternative views of maladaptive sustainment of brain patterns have also been proposed. All of these patterns can benefit from the method of the invention.

Sleep disorders are characterized by altered brain rhythms. For example, in many cases, schizophrenics that report poor sleep also have an absence of sleep spindles (i.e., a repeating pattern of neural activity that lasts 1-3 seconds and that is crucially dependent on thalamic bursting). A clear therapeutic target for increasing sleep maintenance is the enhancement of appropriate thalamic bursting. Such enhancement can be achieved by using the methods of the invention.

Vascular regulation is implicated in a wide variety of diseases, e.g., vascular disease, diabetes, vasospasm, Alzheimer's Disease, vascular dementia, stroke, and hypertension. Impaired vascular dynamics are implicated in these conditions. Enhancing calcium wave propagation in smooth muscle can improve vascular tone and the expression of dynamics processes (e.g., dilation or constriction). In the brain, enhancing astrocytic calcium wave propagation can similarly enhance the control of vascular dynamics, as this cell type and this process are both implicated strongly in vascular tone.

In pulmonary control (e.g., peristalsis) and in diseases or conditions of hollow organs (e.g., asthma), enhancing smooth muscle calcium function by sensing highly localized signals obtained through the use of localized luminescent proteins or conjugates described herein can promote or suppress calcium-driven activities of the cell (e.g., relaxation or constriction). Cytoplasmic entry of $Ca^{2+}$ is a key driver of contractile behavior in smooth muscle, while $Ca^{2+}$ flux in several smooth muscle micro-domains can have complex effects (e.g., compensatory relaxation of pressure-driven constriction in arteries). Thus, enhanced control of calcium dynamics in smooth muscle localized to specific channels and specific subcellular elements may be of therapeutic value. In a non-limiting example, a conjugate including a luminescent protein and a voltage-gated ion channel can be expressed can be co-expressed with CatCh, a light-gated ion channel permitting that admits high flux of calcium, or iC1C2, a hyperpolarizing agent that would be expected to suppress voltage-dependent calcium channel opening.

In forms of diabetes, insufficient insulin is produced by pancreatic beta cells (PBC), leading to high blood glucose. To enhance insulin production by glucose-stimulated calcium oscillations, luciferases or their conjugates with light-gated ion channels, as described herein, can be targeted to insulin vesicles and conjugates generated by fusing a calcium-sensing luminescent protein or a conjugate thereof (e.g., a conjugate including a light-gated ion channel) to a voltage-gated ion channel (e.g., Cav1.3 channel or related channels that mediate calcium entry in these cells). Calcium-triggered light emission will enhance the probability of oscillatory calcium action potentials, thereby enhancing insulin release. Light-gated ion channels can not only depolarize cells but also admit calcium, a useful tool in systems where voltage-gated calcium channels are down-regulated, such as when glucose is chronically elevated. Hyperpolarizing agents can conversely suppress calcium oscillations and insulin release.

In smooth muscles, sensing calcium that enters the cell from the extracellular space with a luminescent protein or a conjugate thereof (e.g., a conjugate including a light-gated ion channel) positioned near the cytoplasmic face of the ion pore of the smooth muscle isoform of Cav1.2 channels would be expected to lead to light generation activating a light-gated ion channel, thereby reducing or amplifying the probability of the secondary event. For example, curtailing or augmenting calcium entry through plasma membrane Cav1.2 channels and thereby curtailing or augmenting calcium-induced calcium release from the sarcoplasmic reticulum). Attenuation or enhancement of this signaling pathway may in turn regulate muscle contraction.

Desynchronization of excitable cells can be achieved using methods and compositions described herein. For example, excitable cells expressing (e.g., heterogeneously expressing) a luminescent protein and a light-gated ion channel can be desynchronized by the action of a luciferin, whereby oxidation reaction of the luciferin mediated by the luminescent protein produces light, which then modulates the activity of the light-gated ion channel by being absorbed. In a non-limiting example, synchronous calcium burst production is often associated with failed motor initiation in Parkinson's Disease. If bioluminescent light production depends on the large calcium influxes observed under such conditions, then once a synchronous burst is observed across cells, light will be produced by a subset of those cells. They will then be expected to rapidly and effectively impact those that also express a light-gated ion channel, weakly and slowly impact those that express a light-gated ion channel but not a luminescent protein, and will not substantially impact (at least not through light production) those that do not express light-gated ion channels. Implementation of this strategy could also include use of a second luminescent protein and a second light-gated ion channel. These additional elements could do the opposite of the first luminescent protein and the first light-gated ion channel, thereby combinatorially enhancing heterogeneity. As an example, a first luminescent protein could produce light of a first wavelength that is optimal for driving a first light-gated ion channel (e.g., a depolarizing element) tuned to absorb light of the first wavelength. A second luminescent protein could emit light of a second wavelength that is optimal for driving a second light-gated ion channel (e.g., a hyperpolarizing element) tuned to absorb light of the second wavelength. The expression of each of these four elements independently in a body region (e.g., among adjacent smooth muscles or in a brain nucleus) would enhance a desynchronizing effect. Cells that express the first light-gated ion channel would be, e.g., depolarized with luciferin presentation, with at least two classes of cells, those that also expressed the first luminescent protein, and those that did not. Cells that express only the second light-gated ion channel would similarly have at least two types of depolarizing responses. In this scenario, cells that expressed both of the first and the second light-gated ion channels may have several levels of response: if they expressed only the first luminescent protein, they would be strongly depolarized but weakly hyperpolarized, reaching an intermediate membrane potential only achieved by expression of both light-gated ion channels.

Similarly, coherence of intracellular activity (e.g., propagating action potential, calcium spike, or subthreshold signal may be disrupted by localizing a luminescent protein and a light-gated ion channel to different regions within a cell (e.g., soma, dendrites, or axon in a neuron).

Luminescent Proteins

Luminescent proteins that may be used according to the methods of the invention can be those known in the art and can include a luciferase (e.g., a *Gaussia* luciferase, a *Metridia* luciferase, *Renilla*-luciferin 2-monooxygenase, or a firefly luciferase) or a photoprotein (e.g., Aequorin or Obelin). The luciferase or photoprotein can be wild-type or mutant, e.g., Aequorin D119A or Aequorin A119/D28L. A luminescent protein can be selected based on its brightness to control the extent of desirable modulation. For example, modulation of the activity of a light-gated ion channel disposed in a cell different from the cell expressing the luminescent protein would require a brighter luminescent protein, whereas, for the modulation of the activity of a light-gated ion channel disposed in the same cell, a dimmer luminescent protein would suffice.

A luminescent protein may be localized within a cell (e.g., intracellularly or extracellularly). In a non-limiting example, a luciferase (e.g., a pH-sensitive luminescent protein) may be localized in the extracellular space of the synapse. In a non-limiting example, pH-sensitive luminescent protein in the synapse can sense synaptic events by the change in the local acidic environment during/after synaptic release. In this context, light production and therefore cellular control would be expected to be engaged when a synapse was active but not when the cell was generically changed in its activity levels.

Direct activation of an extracellular luminescent protein by only a luciferin—for those light production molecules that do not depend on a secondary factory like calcium—if localized to a presynaptic axon terminal could drive enhanced release of neurotransmitter in a specific, genetically targeted cell type (e.g., dopaminergic cells) without requiring the production of an action potential. Conversely, suppression of release could be achieved only in specific synapse types while allowing normal action potential production.

Ion-Binding Domain

The luminescent protein can be modified to enhance ion concentration sensitivity of the luminescent proteins. For example, a *Gaussia* luciferase can be modified to incorporate a domain that is conformationally sensitive to the concentration of an ion (e.g., $Ca^{2+}$) of interest. One non-limiting example of such domain is calmodulin; thus, a split *Gaussia* luciferase (e.g., a *Gaussia* luciferase split at G88/G89 or G93/E94) can be spliced with the CAM-M13 $Ca^{2+}$-binding domain. Calmodulin is a $Ca^{2+}$-binding protein that undergoes a conformation change upon binding $Ca^{2+}$ ions. Inclusion of the $Ca^{2+}$-binding domain of calmodulin in a lucifersa can render the luciferase $Ca^{2+}$-sensitive or increase $Ca^{2+}$-sensitivy of the luciferase. In particular, the luciferase can be split, such that the chromophore of the luciferase is either perturbed by the split or is also split between the two portions of the luciferase. Thus, calmodulin domain spliced between the two portion of the luciferase can reconstitute the chromophore of the luciferase upon binding $Ca^{2+}$ ions through conformational change of the calmodulin $Ca^{2+}$-binding domain, thereby allowing for light emission by the luciferase. Upon decoordination of $Ca^{2+}$ ions, the ensuing conformation change of the calmodulin $Ca^{2+}$-binding domain also disassembles the chromophore of the luciferase, thereby inhibiting luminescence in the absence of $Ca^{2+}$.

Fluorescent Protein

The luminescent protein can further include a fluorescent protein (e.g., a Green Fluorescent Protein, a Red Fluorescent Protein, or a Yellow Fluorescent Protein or a modification thereof) known in the art. Non-limiting examples of modified fluorescent proteins include tdTomato, mCherry, and Venus. Inclusion of a fluorescent protein in the luminescent protein can provide the flexibility of choosing an appropriate wavelength to match the peak excitation wavelength of the light-gated ion channel. Without being bound by a theory, a luminescent protein containing a fluorescent protein and either luciferase or photoprotein can convert chemical energy through oxidation reaction mediated by the luciferase or photoprotein into emission of light by the fluorescent protein. The energy required for the emission can be provided through fluorescence resonance energy transfer (FRET) between the fluorescent protein and either luciferase or photoprotein.

Targeting Moiety

The luminescent protein can include a targeting moiety that targets the protein to a specific subcellular compartment (e.g., dendritic postsynaptic density). Targeting moieties for subcellular compartments are known in the art. Non-limiting examples of targeting moieties include polypeptide ESDV (SEQ ID NO: 1) (from GluN2B) and polypeptide IYHKVKRVIEDL (SEQ ID NO 2). Each of these peptides binds PSD-95. Including a targeting moiety in the luminescent protein allows for greater control over the desired location of the luminescent protein. In particular, when the cells expressing the luminescent protein and the light-gated ion channel are different, the use of a targeting moiety in the luminescent protein can help to locate the luminescent protein closer to the light-gated ion channel expressed on a different cell.

Localization to Subcellular Elements

Luminescent proteins can be localized within a cell by linking (e.g., covalently or non-covalently) them directly to subcellular elements (e.g., channels) that produce or consume factors capable of inducing or enhancing light production by the luminescent protein. Alternatively, luminescent proteins can be localized within a cell through the use of a targeting moiety. A non-limiting example of the factor is a nucleoside triphosphate (e.g., ATP). Methods of the invention can allow for local metabolic control in the cell by covalently linking a nucleoside triphosphate-dependent luminescent protein to a molecule that consumes or produces a nucleoside triphosphate. Non-limiting examples of molecules that consume or produce ATP include adenylate cyclase. ATP can be produced from adenosine diphosphate or adenosine monophosphate and various phosphate group donors by a variety of enzymes including ATP synthase.

The luminescent protein (e.g., a $Ca^{2+}$-sensitive luciferase or a photoprotein (e.g., Aequorin)) can be localized (e.g., conjugated) to a voltage-gated ion channel (e.g., a Cav channel (e.g., a neuronal form of Cav1.2 that is enriched at postsynaptic sites (GENBANK: AY728090), Cav1.3 that is enriched in certain postsynaptic neurons (Addgene plasmid #49333), Cav2.2 that is enriched at presynaptic sites (GENBANK AF222337), or Cav2.2 that is enriched at presynaptic sites in nociceptors (GENBANK AF222337). In neurons, the Cav channel may be, e.g., one of the nine different Cav channel subtypes (e.g., Cav1.2 (postsynaptic/dendritic), Cav1.3 (postsynaptic/dendritic and somatic) Cav2.1 (presynaptic), Cav2.2 (presynaptic), and Cav3.3 (postsynaptic/dendritic and somatic)). In astrocytes, the Cav channel may be, e.g., Cav2.2, Cav1.2, Cav1.3, Cav2.3, and Cav3.1. In smooth muscle, such calcium channels could be Cav1.2 and Cav1.3, in cardiac muscle Cav1.2, and in skeletal muscle Cav1.1. In some embodiments, the Cav channel is Cav1.2, Cav2.1, or Cav3.3. Such conjugates can enhance the $Ca^{2+}$-concentration sensitivity of the luminescent protein. Without being bound by a theory, tethering a calcium-sensitive luminescent protein to a specific channel would produce a bioluminescent reaction only in a specific voltage of an excitable cell (e.g., neurons, muscle cells, heart cells, and endocrine cells) as calcium channels typically operate within specific voltage ranges. Non-limiting applications of such specific voltage activation would be amplifying or suppressing the activity of a cell or transiently changing the cell's membrane trajectory. For example, from Cav3 channels start to open at relatively negative membrane voltages approximately −70 mV through to Cav1.1 channels that require strong depolarizations to activate (approximately 0 mV).

A subcellular element can be further fused (e.g., at the carboxy-terminus) to a fluorescent protein known in the art (e.g., those described above), or to a Myc or His tag for cellular visualization and biochemical immunoprecipitation experiments.

As a result of placing the luminescent protein adjacent to the subcellular element that produce changes in a concentration of a molecule that controls light production by the luminescent protein, the luminescent protein will effectively be placed in the position of the highest concentration of the molecule within or outside of the cell. A non-limiting example of this approach involves placing luminescent proteins next to the pores of the channels, as calcium fluctuations are highest at the pores of channels allowing for greater detection accuracy.

Localization of a luminescent protein adjacent to a voltage-gated ion channel or other subcellular element can allow for sensing and response to signals before they propagate within the cell resulting in attenuation or amplification of signals. Non-limiting examples of calcium entry being crucial to the function of excitable cells are generation of action potentials and plasticity in neurons (e.g., propagation of calcium spikes in large pyramidal neurons), and propagation of calcium waves crucial to astrocyte signaling to neurons, astrocytes, and blood vessels in astrocytes.

Localization of a luminescent protein close to a calcium pore can allow for either the quenching of neural calcium spikes or glial waves before the initiation or escalation of the probability of a calcium spike or astrocytic calcium waves occurring more effectively propagating via opening appropriate light-gated channels adjacent to and in close proximity to initiating events.

The principle of enhanced or suppressed propagation can encompass multi-cellular events in addition to intracellular events. Non-limiting examples of multi-cellular events can be spreading calcium waves that astrocytes and muscles are known to display. Highly localized sensing of the calcium events that initiate such events in a single cell would aid in the probability of propagation between cells also, both through enhancing intracellular propagation and potentially through light transmission to neighboring cells that possess optogenetic elements.

This technology can be applied to provide feedback amplification or attenuation of a signal within a given signaling complex that utilize second messengers (e.g., calcium, IP3, cAMP, etc.) without interfering globally with cell function. A non-limiting example can be utilization of calcium by spatially segregated signaling networks within individual cells to initiate or control different cell functions (e.g., an increase in calcium concentration triggering transmitter release in presynaptic terminals while regulating the density of receptors and synaptic plasticity in postsynaptic dendrites).

Conjugation to Light-Gated Ion Channel

The luminescent protein can be conjugated to a light-gated ion channel. When the luminescent protein is conjugated to a light-gated ion channel, the same luminescent protein is not conjugated to a voltage-gated ion channel. Likewise, when the luminescent protein is conjugated to a voltage-gated ion channel, the same luminescent protein is not conjugated to a light-gated ion channel. The light-gated ion channels that can be conjugated to the luminescent protein can be those known in the art, in particular, can be those discussed herein.

Alternatively, a conjugate (e.g., a fusion protein) that combines a luminescent protein (e.g., calcium-sensitive luminescent protein), a light-gated ion channel, and a subcellular element (e.g., the voltage-gated calcium channel) can be the optimal configuration for enhancing sensitivity of the optogenetic response to a change in a local concentration of a molecule (e.g., a calcium ion or a nucleoside triphosphate) that induces or enhances luminescence of the luminescent protein. Without being bound by a theory, this enhancement may be attributed to shorter distances between the calcium sensing luminescent protein and both of the pore of the channel and the optogenetic element. Advantageously, the short distances may enhance an event detection and response specificity.

Localization of a luminescent protein close to a light-gated channel can allow for local sensing of events and responding without driving responses in distal cells, even on subcellular level.

Linkers

Short peptide linkers can be used to connect the luminescent protein to either a voltage-gated ion channel or a light-gated ion channel (e.g., linkers of from 4 to 50 amino acids (e.g., GDPLVQCGGIAGSAT (SEQ ID NO:3) or (SGGSGSGGQ)$_5$SGLRS (SEQ ID NO: 4), e.g., when the luminescent protein contains Aequorin). In a non-limiting example, a short peptide linker (e.g., GDPLVQCG-GIAGSAT (SEQ ID NO: 3)) can be used to fuse a luminescent protein and, optionally, a light-gated ion channel to the C- or N-terminus of the Cav channel (e.g., Cav2.2 channel). Alternatively or additionally, such short peptide linkers can be used to connect domains within the luminescent protein (e.g., to connect a luciferase to a targeting moiety, to connect a luciferase to a fluorescent protein, etc.)

Any modification to the luminescent protein described herein can be performed according to methods known in the art.

Luciferin

Luciferin that may be used in the methods of the invention includes those known in the art. Non-limiting examples of luciferin include coelenterazines (e.g., native coelenterazine, coelenterazine cp, coelenterazine f, coelenterazine h, coelenterazine 400a, coelenterazine i, coelenterazine n, and methyl coelenterazine), vargulin, bacterial luciferin, firefly luciferin, snail luciferin, and dinoflagellate luciferin.

Luciferin can be produced by a cell in a tissue. For example, a tissue can be modified using transfection, transduction, or transgenic methods known in the art to express a luciferin or a precursor for a luciferin. Heterologous expression of pre-coelenterazine peptide and subsequent isolation of coelenterazine are described in U.S. Pat. No. 5,741,668, the nucleic acids and peptides of which are incorporated herein by reference.

Luciferin can be administered to a mammal parenterally as a pharmaceutical composition. Parenteral administration may include intramuscular, intravenous, intraarterial, intracranial, subcutaneous, intraorbital, intraventricular, intraspinal, intrathecal, intraperitoneal, rectal, and topical routes of administration. Topical route of administration may include transdermal, intradermal, intranasal, intrapulmonary, buccal, and sublingual routes of administration. The pharmaceutical compositions are formulated according to the selected route of administration. Parenteral administration may be by continuous infusion over a selected period of time. The compounds desirably are administered with a pharmaceutically acceptable carrier. Pharmaceutical formulations of the compounds described herein formulated for treatment of the disorders described herein are also part of the present invention.

A pharmaceutical composition of luciferin can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of suspensions, emulsions, solutions, or lyophilized powder. As is known in the art, the type of diluent can vary depending upon the intended route of administration. The resulting compositions can include additional agents, e.g., preservatives.

The excipient or carrier is selected on the basis of the mode and route of administration. Suitable pharmaceutical carriers, as well as pharmaceutical necessities for use in pharmaceutical formulations, are described in *Remington: The Science and Practice of Pharmacy*, 22$^{nd}$ Ed., Loyd V. Jr., Lippencott Williams & Wilkins (2012), a well-known reference text in this field, and in the USP/NF (United States Pharmacopeia and the National Formulary). Examples of suitable excipients include water. Other exemplary excipients are described in *Handbook of Pharmaceutical Excipients*, 6th Edition, Rowe et al., Eds., Pharmaceutical Press (2009).

The pharmaceutical composition may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. For example, to prepare such a composition, the compounds of the invention may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate. Additional information regarding parenteral formulations can be found, for example, in the United States Pharmacopeia-National Formulary (USP-NF), herein incorporated by reference.

The parenteral formulation can be any of the five general types of preparations identified by the USP-NF as suitable for parenteral administration:

(1) "Drug Injection": a liquid preparation that is a drug substance or a solution thereof;
(2) "Drug for Injection": the drug substance (e.g., luciferin as a dry solid that will be combined with the appropriate sterile vehicle for parenteral administration as a drug injection;
(3) "Drug Injectable Emulsion": a liquid preparation of the drug substance that is dissolved or dispersed in a suitable emulsion medium;
(4) "Drug Injectable Suspension": a liquid preparation of the drug substance suspended in a suitable liquid medium; and
(5) "Drug for Injectable Suspension": the drug substance as a dry solid that will be combined with the appropriate sterile vehicle for parenteral administration as a drug injectable suspension.

Exemplary formulations for parenteral administration include solutions of the compound prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in *Remington: The Science and Practice of Pharmacy*, 22nd Ed., Loyd V. Jr., Lippencott Williams & Wilkins (2012) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the compound. Exemplary formulations for parenteral release of the compound include: aqueous solutions, powders for reconstitution, cosolvent solutions, oil/water emulsions, suspensions, oil-based solutions, liposomes, microspheres, and polymeric gels.

Light-Gated Ion Channels

Non-limiting examples of light-gated ion channels include channelrhodopsins, halorhodopsins, archaerhodopsins, and melanopsins, their natural variants, engineered chimeras and variants, and humanized variants (e.g., specific non-limiting examples of light-gated ion channels are provided in Table 1).

TABLE 1

| Channel Acronym | Name of channel | Organism from which channel was isolated | Peak Excitation Wavelength (nm) | Type of Channel | Open/Close |
|---|---|---|---|---|---|
| ChR1 | Channelrhodopsin1 | *Clamydomonas reinhardti* | 470 | Ion channel (H+, Na+, K+, Ca2+) | Open by blue light |
| ChR2 | Channelrhodopsin2 | *Clamydomonas reinhardti* | 470 | Ion channel (H+, Na+, K+, Ca2+) | Open by blue light |
| vChR1 | Channelrhodopsin1 | *Volvox carteri* | 570 | Ion channel (H+, Na+, K+, Ca2+) | Open by yellow light |

TABLE 1-continued

| Channel Acronym | Name of channel | Organism from which channel was isolated | Peak Excitation Wavelength (nm) | Type of Channel | Open/Close |
| --- | --- | --- | --- | --- | --- |
| vChR2 | Channelrhodopsin2 | *Volvox carteri* | 470 | Ion channel (H+, Na+, K+, Ca2+) | Open by blue light |
| ChR2H134R | Channelrhodopsin2 (mutant) | *Clamydomonas reinhardti* | 450 | Ion channel (H+, Na+, K+, Ca2+) | Open by blue light |
| ChR2E123T (ChETA) | Channelrhodopsin2 (mutant) | *Clamydomonas reinhardti* | 490 | Ion channel (H+, Na+, K+, Ca2+) | Open by blue light (faster deactivation) |
| ReaChR | Channelrhodopsin1 (chimera) | *Clamydomonas reinhardti* and *Volvox carteri* | 590-630 | Ion Channel ($Ca^{2+}$) | Open by red light |
| C1V1 | Channelrhodopsin1 (chimera) | *Clamydomonas reinhardti* and *Volvox carteri* | 500-600 | Ion Channel ($Ca^{2+}$) | Open by yellow light |
| ChD | Channelrhodopsin 1/2/hybrid | *Clamydomonas reinhardti* | 450 | Ion channel (H+, Na+, K+, Ca2+) | Open by blue light |
| ChEF | Channelrhodopsin 1/2/hybrid | *Clamydomonas reinhardti* | 470 | Ion channel (H+, Na+, K+, Ca2+) | Open by blue light |
| ChIEF | Channelrhodopsin 1/2/hybrid | *Clamydomonas reinhardti* | 450 | Ion channel (H+, Na+, K+, Ca2+) | Open by blue light |
| ChR2C128A | Channelrhodopsin2 (mutant) | *Clamydomonas reinhardti* | 470 (open)/542 (close) | Ion channel (H+, Na+, K+, Ca2+) | Step function (open by blue light and close by yellow light) |
| ChR2C128S | Channelrhodopsin2 (mutant) | *Clamydomonas reinhardti* | 470 (open)/542 (close) | Ion channel (H+, Na+, K+, Ca2+) | Step function (open by blue light and close by yellow light) |
| ChR2C128T | Channelrhodopsin2 (mutant) | *Clamydomonas reinhardti* | 470 (open)/542 (close) | Ion channel (H+, Na+, K+, Ca2+) | Step function (open by blue light and close by yellow light) |
| NpHR | Halorhodopsin | *Natromonas pharaonis* | 570 | Chloride | Open by yellow light for inhibition |
| eNpHR 2.0 | engineered Halorhodopsin | *Natromonas pharaonis* | 570 | Chloride | Open by yellow light for inhibition |
| eNpHR 3.0 | engineered Halorhodopsin | *Natromonas pharaonis* | 570 | Chloride | Open by yellow light for inhibition |
| Arch 3.0 | Archaerhodopsin | *Halorubrum sodomense* | yellow light | Proton pump | Open by yellow light for inhibition |
| Arch T 3.0 | Archaerhodopsin | *Halorubrum sodomense* | yellow light | Proton pump | Open by yellow light for inhibition |
| Mac 3.0 | Outward light-gated proton pump | *Leptosphaeria maculans* | 542 | Proton pump | Open by yellow light for inhibition |

The light-gated ion channels described herein can be modified by addition of recombinant endoplasmic reticulum export and trafficking signal for improved cell surface expression. The light-gated ion channels can be conjugated to a luminescent protein (e.g., as a fusion protein).

Channelrhodopsin

The light-gated ion channel can be a channelrhodopsin, e.g., ChR1, ChR2, VChR1, ChR2 C128A, ChR2 C128S, ChR2 C128T, ReaChR, C1V1, ChD, ChEF, ChF, or ChIEF. Channelrhodopsins (ChRs) originate from microalgae. The Vitamin A derivative retinal is linked to a lysine residue of the proteins (Retinal Schiff Base, RSB) constituting the light absorbing chromophore. They are activated by blue light. The blue light can have a wavelength of approximately 470 nm (e.g., 440, 450, 460, 470, 480, 490 nm). Light absorption causes retinal isomerization around the 13-bond. This isomerization triggers subsequent conformational changes of the protein and gating of the channel. Thermal relaxation of the proteins closes the channel and the protein converts under re-isomerization of the retinal back to the dark state.

ChR2 from *Chlamydomonas reinhardtii* has been established as the ChR prototype for optogenetic application since its expression is more than 10 times superior in most host cells than that of ChR1. Channelrhodopsin can be vChR1 or vChR2 derived from *Volvox carteri*. Channelrhodopsin can be ReaChR, which is a chimera of ChR1 and vChR1. Variants of channelrhodopsins are listed in Table 1.

Channelrhodopsin can be a humanized ChR2 with two mutations (E123T and H134R), and is called ChETA. ChETA has faster deactivation kinetics and faster recovery from inactivation. Channelrhodopsin can be a step function opsin (SFO) with bi-stable excitation that is engineered by a point mutation of ChR2, e.g., ChR2 C128A, ChR2 C128S, and ChR2 C128T. Each of these channels is opened by presenting blue light (470 nm), and the channels can be closed by shining a pulse of green light (542 nm). SFOs allow opening and closing the channel by shining light of different wavelengths, thus providing precise temporal control over the polarization of an excitable cell. Channelrhodopsin can be a stabilized step-function opsin (SSFO) that is engineered by making two mutations in ChR2 (C128S and D156A). The SSFO channel has a more stabilized conducting state with a time constant of nearly 30 minutes following a brief pulse of activating light. The SSFO may be closed using yellow light (590 nm).

Halorhodopsin

A light-gated ion channel can be a halorhodopsin, e.g., NpHR, eNpHR 2.0, and eNpHR 3.0. Halorhodopsins are originate from halobacteria and are activated by yellow (or amber) light of approximately 570 nm wavelength (e.g., 540, 550, 560, 570, or 580 nm). The halorhodopsin from *Natronomonas pharaonis* (NpHR) has been established as the prototype halorhodopsin and has been used for engineering the variants eNpHR 2.0 (Gradinaru et al., *Brain Cell Biol.*, 36: 129-139, 2008) and eNpHR 3.0 (Gradinaru et al., *Cell*, 141:154-165, 2010) described in Table 1. Halorhodopsin can be eNpHR 2.0 made by fusion of the FCYENEV ER export motif from a vertebrate inward rectifier potassium channel to the C-terminus of the NpHR protein. Alternatively, halorhodopsin can be eNpHR 3.0 made by adding the trafficking signal from Kir2.1 to the C terminus of the NpHR protein.

Archaerhodopsin

A light-gated ion channel can be an archaerhodopsin, e.g., Arch, Arch T, and Arch T 3.0. Archaerhodopsins are proton pumps from the archaebacteria *Halorubrum sodomense*, e.g., Arch, and are activated by yellow light. Archaerhodopsin can be Arch T is derived from the *Halorubrum* sp. TP009 strain and is 3.5 times more sensitive than Arch. Archaerhodopsin can be Mac3.0 that is an outward light-gated proton pump from *Leptosphaeria maculans*. Mac3.0 is activated by yellow light.

A channelrhodopsin can be coexpressed with a halorhodopsin to achieve bidirectional control of cell membrane permeability as described in Zhang et al (Zhang et al., *Nature*, 2007, 446(7136):633-639).

Expressing Light-Gated Ion Channels and Luminescent Proteins in Cells

The light-gated ion channels and luminescent proteins (collectively "bioluminescent/optogenetic reagents") used in the present invention can be expressed in excitable cells or its precursors by delivery of recombinant nucleic acid molecules encoding these reagents into the cells. The recombinant nucleic acid molecules are cloned into appropriate expression vectors that contain regulatory elements necessary for expression of the optogenetic reagents. The recombinant nucleic acid molecules can be delivered into cells by any one or more methods known in the art e.g., by a virus, by electroporation, by liposomes, or by transgenic methods. These are described below.

Expression Vectors Containing Recombinant Nucleic Acid Molecule for Expressing Bioluminescent/Optogenetic Reagents in Cells Recombinant nucleic acid molecules encoding the bioluminescent/optogenetic reagents described herein are described below.

Construction of vectors for recombinant expression of bioluminescent/optogenetic reagents for use in the invention may be accomplished using conventional techniques which do not require detailed explanation to one of ordinary skill in the art. For review, however, those of ordinary skill may wish to consult Maniatis et al., in Molecular Cloning: A Laboratory Manual, Cold Spring Harbor Laboratory (NY 1982).

For generation of efficient expression vectors, it is necessary to have regulatory sequences that control the expression of the bioluminescent/optogenetic reagent. These regulatory sequences include promoter and enhancer sequences and are influenced by specific cellular factors that interact with these sequences.

Promoter and enhancer regions have been described in the art. Methods for maintaining and increasing expression of transgenes in quiescent cells include the use of promoters including collagen type I (1 and 2), SV40, and LTR promoters. According to one embodiment of the invention, the promoter is a constitutive promoter selected from the group consisting of: ubiquitin promoter, CMV promoter, JeT promoter (e.g., as described in U.S. Pat. No. 6,555,674, incorporated herein by reference), SV40 promoter, Elongation Factor 1 alpha promoter (EF1-alpha), RSV, Mo-MLV-LTR. Examples of inducible/repressible promoters include: Tet-On, Tet-Off, Rapamycin-inducible promoter, and Mx1.

The promoter can be constitutive or inducible tissue-type specific promoter knwon in the art. A non-limiting example of a neuron-specific promoter is synapsin (e.g., hSyn). Non-limiting examples of promoters specific to endothelial cells include: a family of receptor tyrosine kinase genes specifically expressed in mammalian endothelial cells, including Tie1 and Tie2 (also called Tek) (Dumont et al., *Oncogene*, 7:1471-1480, 1992; Schnurch and Risau, *Development*, 119:957-968, 1993), fms-like tyrosine kinase-1 (FLT-1) (Nicklin et al., *Hypertension*, 38:65-70, 2001), intercellular adhesion molecule 2 (ICAM-2) (Cowan et al., *Transplantation*, 62:155-160, 1996), VE-cadherin (VECD) (Hisatsune et al., *Blood*, 105:4657-4663, 2005), Endothelial cell-specific molecule 1 (ESM1) (Lassalle et al., *J. Biol. Chem.* 271:20458-20464, 1996) and synthetic variants thereof.

In addition to using viral and non-viral promoters to drive transgene expression, an enhancer sequence may be used to increase the level of transgene expression. For example, collagen enhancer sequences may be used with the collagen promoter 2 (I) to increase transgene expression. In addition, the enhancer element found in SV40 viruses may be used to increase transgene expression. This enhancer sequence consists of a 72 base pair repeat as described by Gruss et al., *Proc. Natl. Acad. Sci. USA*, 78:943, 1981; Benoist and Chambon, *Nature*, 290: 304, 1981, and Fromm and Berg, *J. Mol. Appl. Genetics*, 1:457, 1982, each of which is incorporated herein by reference. This repeat sequence can increase the transcription of many different viral and cellular genes when it is present in series with various promoters (Moreau et al., *Nucleic Acids Res.*, 9:6047, 1981).

Further expression enhancing sequences include but are not limited to Woodchuck hepatitis virus post-transcriptional regulation element, WPRE, SP163, CMV enhancer, and Chicken β-globin insulator or other insulators.

Transgene expression may also be increased for long term stable expression using cytokines to modulate promoter activity. Several cytokines have been reported to modulate the expression of transgene from collagen 2 (I) and LTR promoters. For example, transforming growth factor (TGF), interleukin (IL)-1, and interferon (INF) down regulate the expression of transgenes driven by various promoters such as LTR. Tumor necrosis factor (TNF) and TGF 1 up regulate, and may be used to control, expression of transgenes driven by a promoter. Other cytokines that may prove useful include basic fibroblast growth factor (bFGF) and epidermal growth factor (EGF).

A collagen promoter with the collagen enhancer sequence (Coll (E)) may also be used to increase transgene expression by suppressing further any immune response to the vector which may be generated in a treated brain notwithstanding its immune-protected status. In addition, anti-inflammatory agents including steroids, for example dexamethasone, may be administered to the treated host immediately after vector composition delivery and continued, preferably, until any cytokine-mediated inflammatory response subsides. An immunosuppression agent such as cyclosporin may also be administered to reduce the production of interferons, which downregulates LTR promoter and Coll (E) promoter-enhancer, and reduces transgene expression.

The expression vector may further include sequences such as a sequence coding for the Cre-recombinase protein, and LoxP sequences. A further way of ensuring temporary expression of the bioluminescent/optogenetic reagent is through the use of the Cre-LoxP system which results in the excision of part of the inserted DNA sequence either upon administration of Cre-recombinase to the cells or by incorporating a gene coding for the recombinase into the virus construct. Incorporating a gene for the recombinase in the virus construct together with the LoxP sites and a structural gene (an bioluminescent/optogenetic reagent in the present case) often results in expression of the structural gene for a period of approximately five days or more.

Virus Mediated Delivery of Expression Vectors to Express Bioluminescent/Optogenetic Reagents in Targeted Cells (e.g., Excitable Cells)

The expression vector containing the recombinant nucleic acid encoding the bioluminescent/optogenetic reagent can be encapsidated within a recombinant virus e.g., recombinant adeno-associated virus (AAV), recombinant retrovirus, recombinant lentivirus, recombinant poxvirus, recombinant rabies virus, recombinant pseudo-rabies virus, recombinant herpes simplex virus, papovavirus, human immunodeficiency virus (HIV), or adenovirus. These viruses are then be administered to the mammal (e.g., a human) so that the targeted cells (e.g., neurons) can be infected by these viruses and the bioluminescent/optogenetic reagents can then be expressed in the targeted cells.

Preferred viruses include lentiviruses and adeno-associated viruses (AAVs). Both types of viruses can integrate into the genome without cell divisions, and both types have been tested in pre-clinical animal studies. Methods for preparation of AAVs are described in the art e.g., in U.S. Pat. Nos. 5,677,158, 6,309,634, and 6,683,058, each of which is incorporated herein by reference. Methods for preparation and in vivo administration of lentiviruses are described in US 20020037281 (incorporated herein by reference). Preferably, a lentivirus vector is a replication-defective lentivirus particle. Such a lentivirus particle can be produced from a lentiviral vector containing a 5' lentiviral LTR, a tRNA binding site, a packaging signal, a promoter operably linked to a polynucleotide signal encoding the fusion protein, an origin of second strand DNA synthesis and a 3' lentiviral LTR.

Retroviruses are most commonly used in human clinical trials, since they carry 7-8 kb and since they have the ability to infect cells and have their genetic material stably integrated into the host cell with high efficiency (see, e.g., WO 95/30761; WO 95/24929, each of which is incorporated herein by reference). Oncovirinae require at least one round of target cell proliferation for transfer and integration of exogenous nucleic acid sequences into the patient.

For use in humans, the retrovirus must be replication defective. This prevents further generation of infectious retroviral particles in the target tissue. Instead the replication defective virus becomes a "captive" transgene stable incorporated into the target cell genome. Typically in replication defective vectors, the gag, env, and pol genes have been deleted (along with most of the rest of the viral genome). Heterologous DNA (in case of the present invention, the recombinant nucleic acid molecule encoding the bioluminescent/optogenetic reagent) is inserted in place of the deleted viral genes. The heterologous genes may be under the control of the endogenous heterologous promoter, another heterologous promoter active in the target cell, or the retroviral 5' LTR (the viral LTR is active in diverse tissues).

The viruses can be introduced into the body by intravascular injection (e.g., intraarterially or intravenously). For localized targeting, virus injection from an IV catheter has already been used to achieve spatially discrete expression (e.g., of a single chamber of the heart or localized cerebral vasculature). In cases where the desired target can be accessed by catheterization, local transduction would then provide spatial specificity to optogenetic control of cell polarization. Alternatively, direct intra-cranial virus injection can be used to target specific vessels. While more invasive than catheterization, this procedure is less invasive than implantation of a deep-brain stimulator and does not require maintenance of hardware in the brain. Further, in cases where more elaborate surgery is already standard—tumor removal, epilepsy surgery—local transduction could be achieved. Alternatively, direct peripheral virus injection can be used to target specific vessels outside of the central nervous system.

Viruses encoding bioluminescent/bioluminescent/optogenetic reagents may be placed into a pharmaceutically acceptable suspension, solution or emulsion. Suitable mediums include saline and liposomal preparations. More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Non-Viral Methods for Delivery of Expression Vectors to Express Bioluminescent/Optogenetic Reagents in Targeted Cells (e.g., Excitable Cells)

The recombinant nucleic acid molecule encoding the bioluminescent/optogenetic reagent may be delivered into target cells by non-viral methods. For example, a colloidal dispersion system may be used for targeted gene delivery. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV), which range in size from 0.2-4.0 µm, can encapsulate a substantial percentage of an aqueous buffer containing large macro molecules. RNA, DNA and even intact virions can be encapsulated within the aqueous interior and be delivered to cells in a biologically active form. For a liposome to be an efficient gene transfer vehicle, the following characteristics should be present: encapsulation of the expression vector at high efficiency with retention of their biological activity; preferential and substantial binding to a target cell in comparison to non-target cells; delivery of the aqueous contents of the vesicle to the target cell cytoplasm at high efficiency; and accurate and effective expression of genetic information.

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Active targeting can involve alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted gene delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Heterogeneous Expression

Heterogeneity of expression across multiple cell types (or cellular positions) can be achieved by a variety of approaches known in the art. Non-limiting examples of methods useful in achieving a heterogeneous expression are provided below.

I. Heterogeneity of expression of a bioluminescent protein (BL) and a light-gated ion channel (OG) can be achieved by injection of virus (e.g., AAV, lenti, HSV, or other viral vectors) carrying the coding sequence for each element under control of a cell-specific or ubiquitous promoter, which results in transduction of cells in the target organ. In the simple case of one bioluminescent protein and one matching light-gated ion channel, a preparation of the two viruses mixed at equal titers (viral genome copies) is injected into the target region. Most cells will be transduced by both populations, some by single populations, and some within the injected site will not be transduced at all.

II. If two different bioluminescent proteins are mixed with two light-gated ion channels, the distribution becomes more complex, with 16 formal possibilities. The majority of cells of the targeted region will still get all four or at least three of the viruses of the mix.

III. Co-injection of two populations of double-inverted (DI) luminescent proteins (DI-BL1-DI-BL2) and light-gated ion channels (DI-OG1-DI-OG2) flanked by recombinase recognition sites (either loxP sites, frt sites, rox sites, or att sites) together with a virus expressing the respective recombinase (Cre, Flp, Dre, PhiC31) or injection of the DI expressing viruses in transgenic mice expressing these recombinases, can result in recombinase-mediated stochastic events resulting in three possible outcomes: expression of the first element (BL1 or OG1), expression of the second element (BL2 or OG2), or expression of neither. Variation in viral transduction of a given cell is reduced to 4 options (as in I.), versus 16 options (as in II.) Another version might contain the respective recombinase in a self-deleting constellation within the DI virus.

IV. In some instances, experimental animals can be genetically engineered to express the desired BL and OG elements in constellations analogous to the designs outlined for viral vectors in I-III.

V. A 'brainbow'-like approach to heterogeneity may also be used in accordance with the methods known in the art.

TABLE 2

| I. | |
|---|---|
| AAV-BL + AAV-OG | AAV-BL + AAV-OG |
| | AAV-BL |
| | AAV-OG |

| II. | |
|---|---|
| AAV-BL1 + AAV-OG1 + AAV-BL2 + AAV-BL2 | AAV-BL1 + AAV-OG1 + AAV-BL2 + AAV-OG2 |
| | AAV-BL1 + AAV-OG1 + AAV-BL2 |
| | AAV-BL1 + AAV-OG1 + AAV-OG2 |
| | AAV-BL1 + AAV-BL2 + AAV-OG2 |
| | AAV-OG1 + AAV-BL2 + AAV-OG2 |
| | AAV-BL1 + AAV-OG1 |
| | AAV-BL2 + AAV-OG2 |
| | AAV-BL1 + AAV-BL2 |
| | AAV-BL1 + AAV-OG2 |
| | AAV-OG1 + AAV-BL2 |
| | AAV-OG1 + AAV-OG2 |
| | AAV-BL1 |
| | AAV-OG1 |
| | AAV-BL2 |
| | AAV-OG2 |

TABLE 2-continued

III.

| | | |
|---|---|---|
| AAV-DI-BL1-DI-BL2 + AAV-DI-OG1-DI-OG2 | AAV-DI-BL1-DI-BL2 + AAV-D1-OG1-DI-OG2 | BL1 + OG1 |
| | | BL1 + OG2 |
| | | BL1 |
| | | BL2 + OG1 |
| | | BL2 + OG2 |
| | | BL2 |
| | | OG1 |
| | | OG2 |
| | AAV-DI-BL1-DI-BL2 | BL1 |
| | | BL2 |
| | AAV-DI-OG1-DI-OG2 | OG1 |
| | | OG2 |

The following examples are meant to illustrate the invention. They are not meant to limit the invention in any way.

EXAMPLES

Example 1: Targeted Expression of a Luminescent Protein

Figure 2:
FIG. 2 is a photograph showing an example in which neocortical neurons in the right hemisphere were transfected with a *Gaussia* luciferase. After intravenous injection of the appropriate luciferin several weeks later (coelenterazine), these cells emitted brightly, allowing localization of the bioluminescence generator through the scalp (IVIS imaging system).

This example demonstrates a targeted expression of *Gaussia* luciferase (GLuc) in mouse brain. Several weeks later, coelenterazine was administered intravenously to the mouse, and an image of the mouse's head was taken with IVIS® imaging system (FIG. 2). As shown in FIG. 2, GLuc was expressed in neocortical cells of right hemisphere only.

Example 2: Hyperpolarization and Depolarization of Neocortical Neurons

Figure 3:
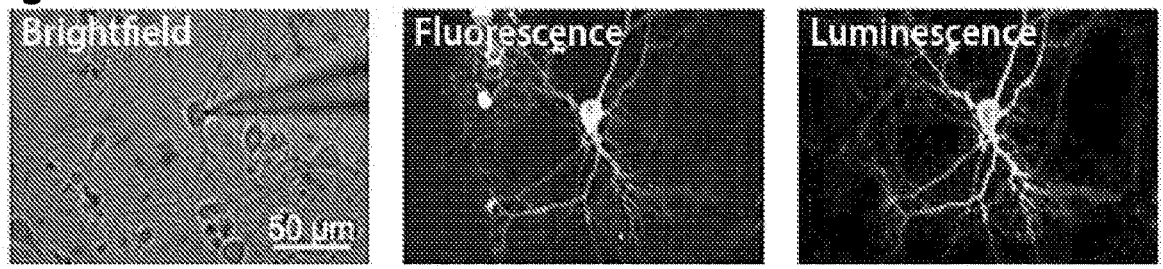
FIG. 3 are three micrographs showing the efficacy in cultured neocortical neurons of the enhanced *Gaussia* Luciferase-VChR1.
Figure 3A:
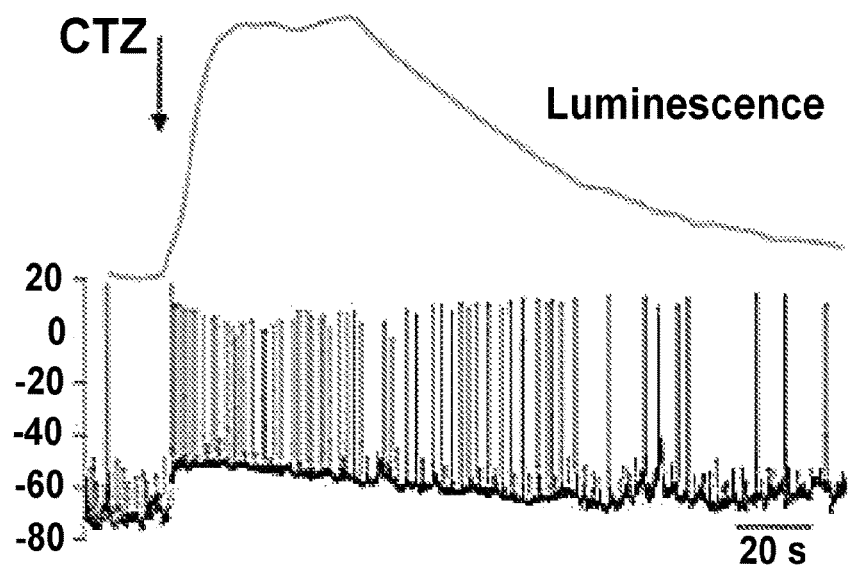
FIG. 3A is a graph showing action potential firing in cultured neocortical neurons expressing enhanced *Gaussia* Luciferase-VChR1.
Figure 3B:
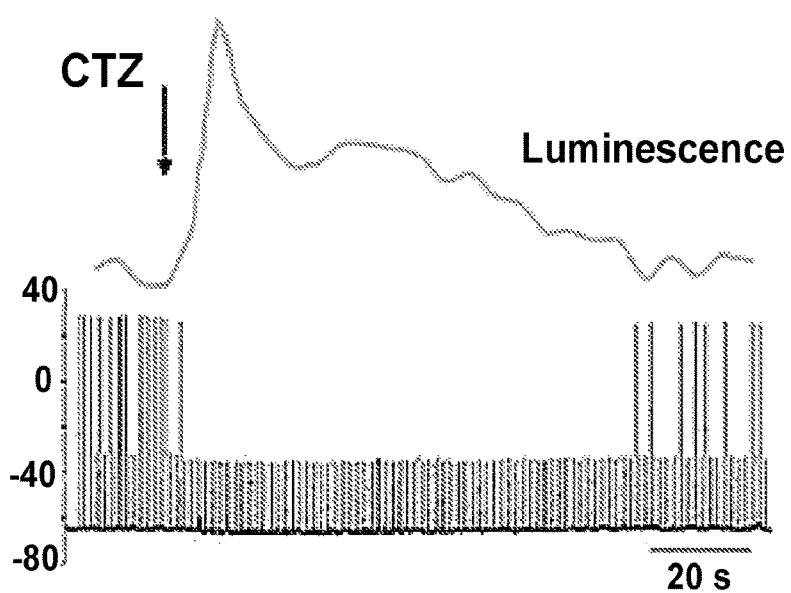
FIG. 3B is a graph showing suppression of spontaneous action potential firing in cultured neocortical neurons expressing *Gaussia* Luciferase-Mac.

This examples demonstrates modulation of neocortical neurons in vitro by contacting the neurons with CTZ. The neurons were modified to express fusion proteins including a luminescent protein (enhanced *Gaussia* luciferase (eGLuc)) and either VChR1 or Mac. Successful expression of the full construct in the neocortical neurons was confirmed by observation of the fluorescence of the reporter protein (upper middle panel titled Fluorescence in FIG. 3). Ability of eGLuc to luminesce was unaffected by the inclusion of light-gated ion channel (VChR1 or Mac), as shown in the upper right panel titled Luminescence in FIG. 3). FIG. 3A (depolarization) shows an increase in spontaneous action potential firing upon contacting CTZ with a cell expressing a fusion protein containing eGLuc-VChR1. FIG. 3B (hyperpolarization) shows a suppression of spontaneous action potential firing upon contacting CTZ with a cell expressing a fusion protein containing eGLuc-Mac.

Figure 4A:
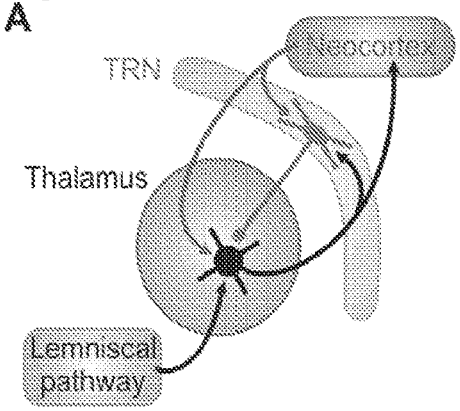
FIG. 4A is a scheme showing the direction of signal propagation from lemniscal axons to neocortex via thalamic reticular nucleus.
Figure 4B:
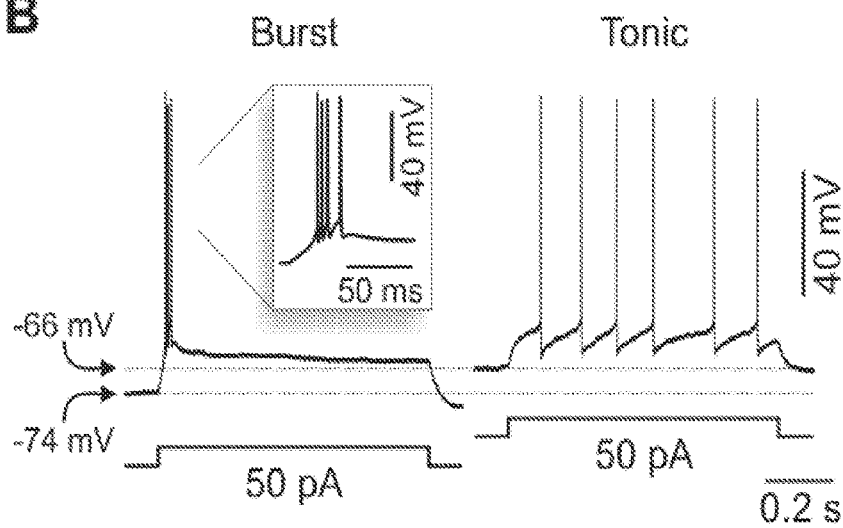
FIG. 4B provides two graphs. The left graph shows hyperpolarization de-inactivating T-type $Ca^{2+}$ channels, permitting large, low-threshold $Ca^{2+}$ spikes that trigger high-frequency bursts of fast $Na^+$-dependent action potentials. The right graph shows depolarization causing inactivation of T-type $Ca^{2+}$ channels and burst suppression; in that case only $Na^+$-dependent action potentials can be evoked by current injection or synaptic excitation.

Example 3: Modulating Excitable Cell Activity by Expressing a Luminescent Protein and a Light-Gated Ion Channel in the Same Cell The use of persistent activity of luminescent protein/light-gated ion channel can be used for burst regulation. This effect can be shown in either single cells, or in cell networks with luminescent proteins expressed in one set of cells and light-gated ion channels in another set of cells. TRN and VPm neurons can be selectively and independently transduced to express a fusion protein containing eGLuc-VChR1 by using methods known in the art. Neurons in brain slices can be visualized in vitro, where high quality current- and voltage-clamp recordings can be made. In particular, the neurons can be neurons in the somatosensory sector of the thalamus, e.g., VPm nucleus and its glutamatergic, excitatory relay neurons, and the adjacent thalamic reticular nucleus and its GABAergic, inhibitory neurons. As shown in FIG. 4A, relay cells receive sensory inputs from lemniscal axons, and the output axons of relay cells. The output axons of relay cells terminate in neocortex, and pass through TRN and form collaterals that excite it. Axons of TRN cells in turn mediate feedback inhibition onto relay cells. TRN cells are also excited by descending excitatory axons from neocortex, and thus also mediate feedforward inhibition on relay cells. Both relay and TRN neurons can generate robust intrinsic spike bursts. As discussed above, thalamic bursting is highly dependent on ongoing membrane potential: Hyperpolarization de-inactivates T-type $Ca^{2+}$ channels, permitting large, low-threshold $Ca^{2+}$ spikes that trigger high-frequency bursts of fast Na+-dependent action potentials. In contrast, a more depolarized membrane potential causes inactivation of T-type $Ca2^+$ channels and burst suppression; in that case only $Na^+$-dependent action potentials can be evoked by current injection or synaptic excitation. An example of these modes of firing is provided in FIG. 4B.

Figure 5A:
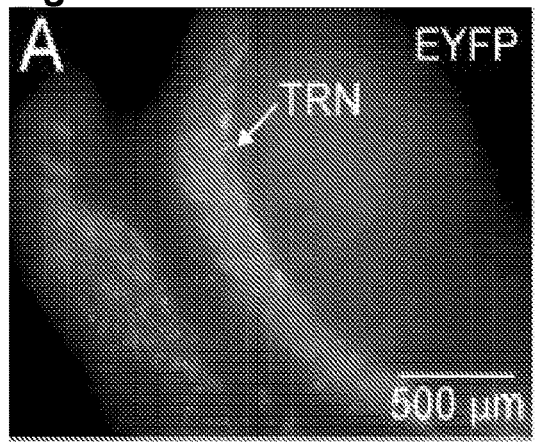
FIG. 5A is a micrograph showing thalamic reticular nucleus (TRN) stereotaxically targeted to express eGLuc-VChR1 by using AAV 2/9-hSyn viral approach.
Figure 5B:
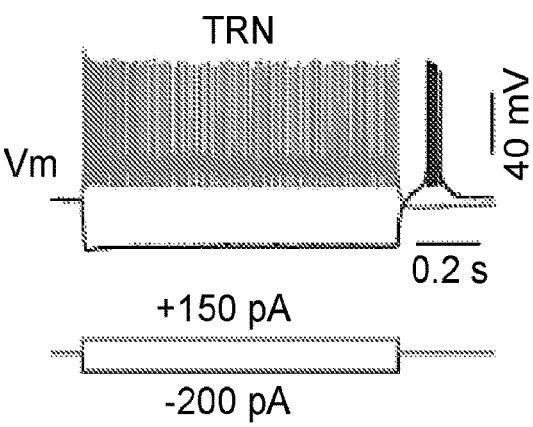
FIGS. 5B and 5C are graphs showing that the transduced TRN neurons were electrophysiologically normal and strongly responsive to LED light pulses. Short latencies and other properties of these responses indicate robust VChR1 expression.
Figure 5C:
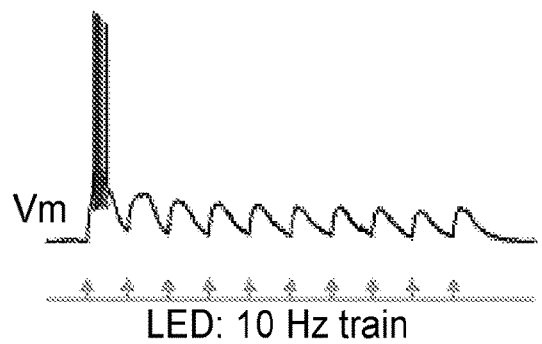
Figure 5D:
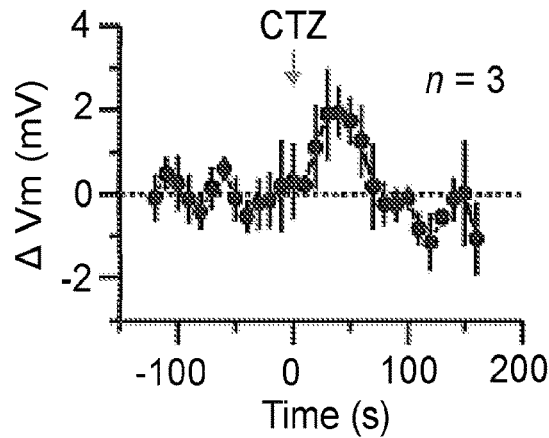
FIGS. 5D and 5E are graphs showing reversible depolarization of ca. 1-3 mV caused by superfusion of coelenterazine (CTZ).
Figure 5E:
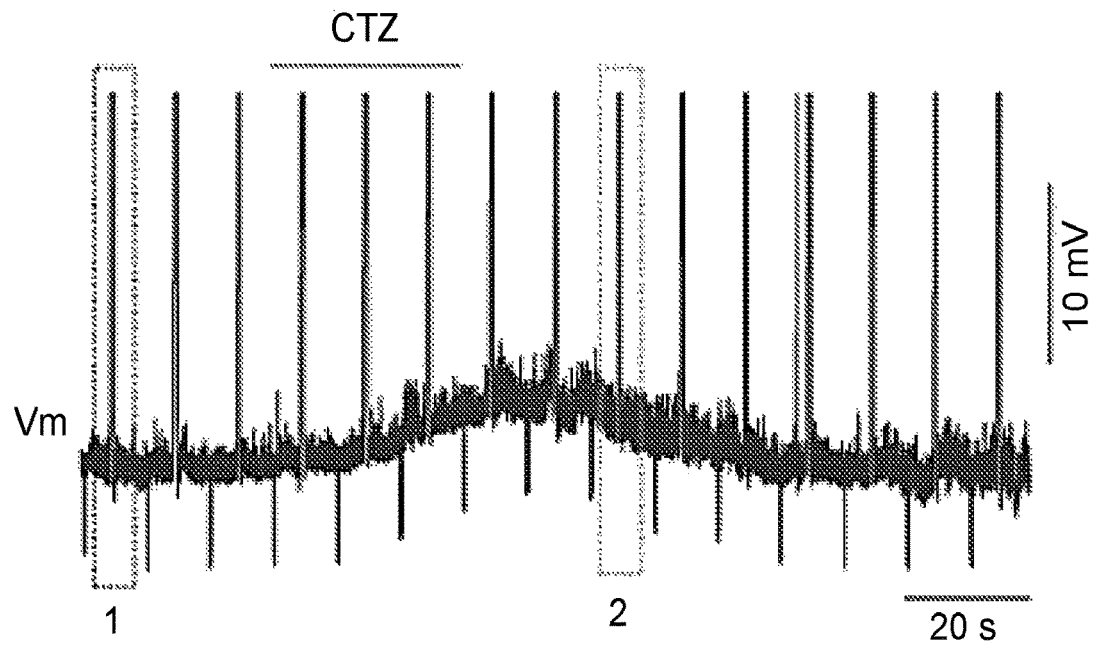
Figure 5F:
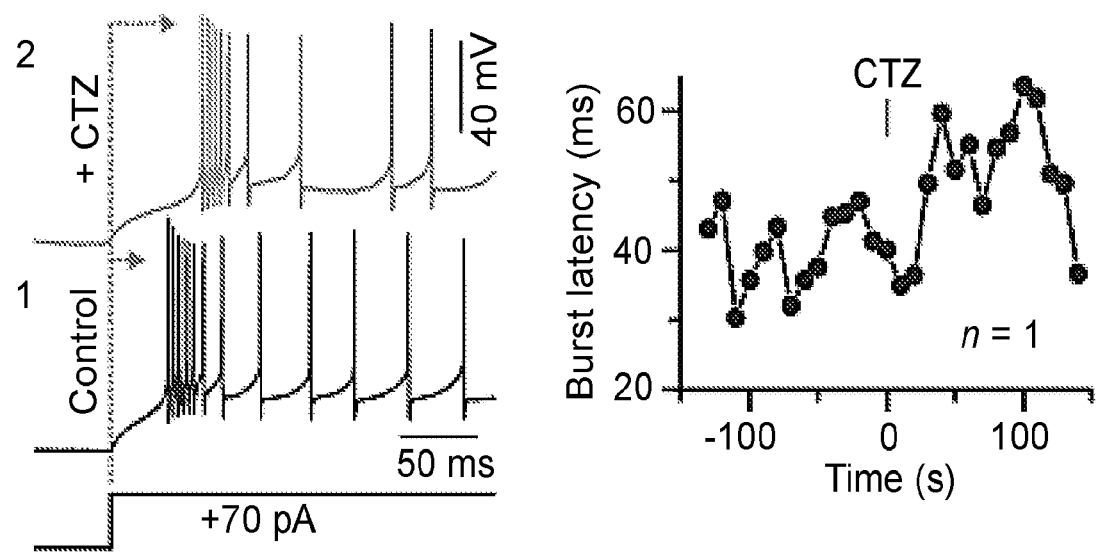
FIG. 5F is a set of graphs showing delay in the onset of stimulus-evoked spike bursts in cells that underwent modest CTZ-evoked depolarization relative to the onset in the control sample.
Figure 6:
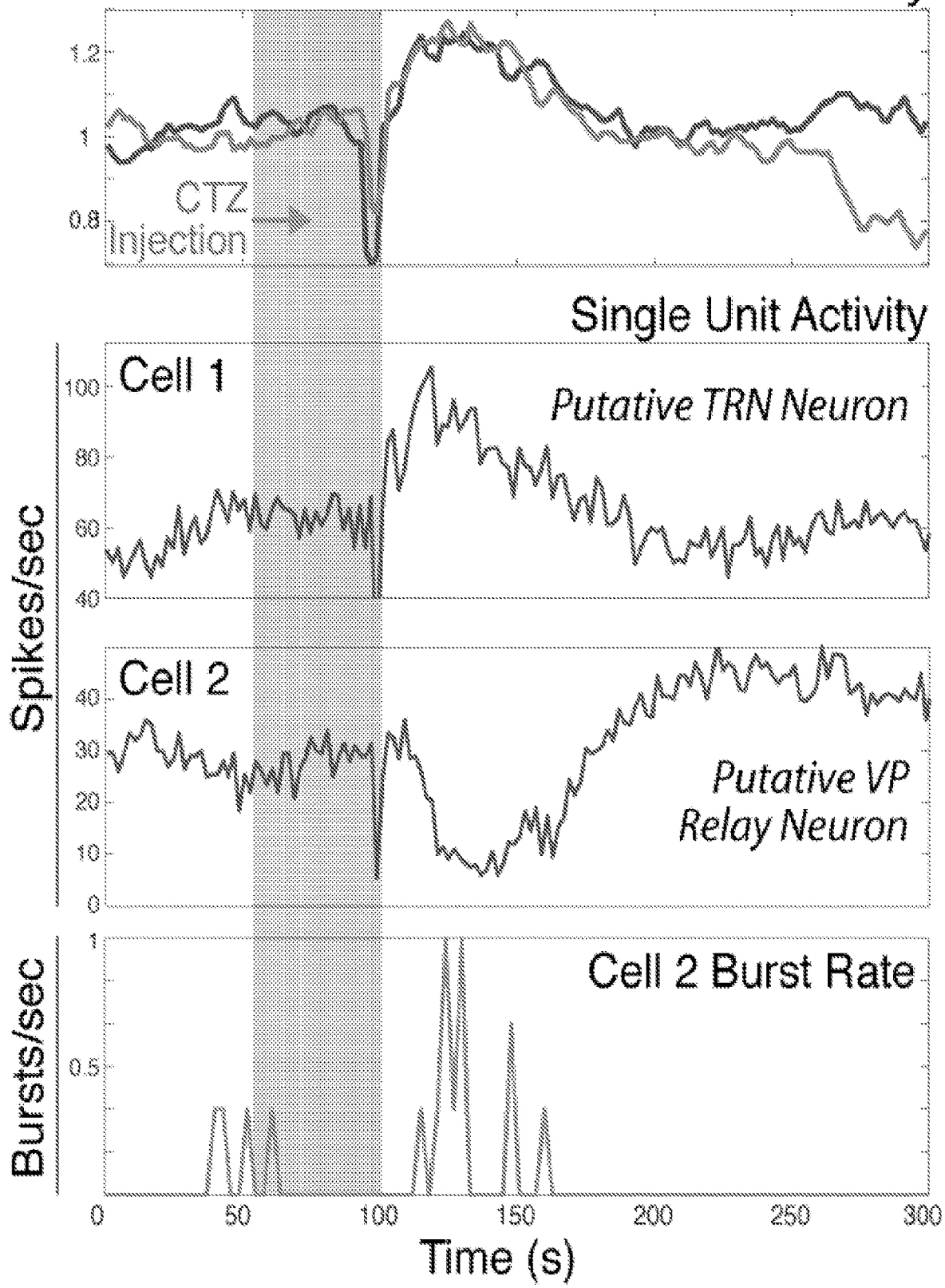
FIG. 6 is a series of charts showing the time course of a multiunit activity (top panel) and single unit activity (bottom three panels) in response to the injection of coelenterazine (CTZ).

Mice were injected with AAV2/9-hSyn-eGLuc-VChR1 into the thalamus of mice, and in vitro slice experiments were performed 7-12 days later. Reporter fluorescence showed strong expression and a specific tropism for TRN in this and other experiments (FIG. 5A). VPm expression was negligible except from TRN axons. Expressing TRN neurons were electrophysiologically normal, and strongly responsive to LED light pulses (FIGS. 5B and 5C). The short latencies and other properties of these responses indicate robust VChR1 expression. Superfusion of the luciferin CTZ (100 μM) caused ca. 1-3 mV reversible depolarization (FIGS. 5D and 5E; N=3 cells, 2 mice). Consistent with the method of the invention, these modest CTZ-evoked depolarizations impacted burst expression, delaying onset of stimulus-evoked spike bursts (FIG. 5F). At 20 days post viral injection, a 16-contact laminar electrode was used to record from the TRN and neighboring relay nuclei under light isoflurane anesthesia (0.5%). The results are shown in FIG. 6. The top panel in FIG. 6 shows the similar time course of multi-unit activity in putative TRN during two injection cycles of CTZ (ca. 150 μg CTZ) IV (tail vein, period of injection in amber). In the multi-unit activity and well-isolated single neurons (e.g., Cell 1), firing increased after CTZ injection, consistent with eGLuc-VChR1 activation and showing a similar time course to CTZ driven responses in vitro (e.g., FIG. 5D). In other cells (e.g., Cell 2, FIG. 6) decreases in firing rate were observed, consistent with relay neurons suppressed by TRN BL-OG activation. Spike shape also indicated relay neuron and not TRN identity. In Cell 2, an increase in burst rate (defined as events with 100 msec prior inactivity and >95 Hz spike rate) was further observed, despite the decrease in overall firing rate. These combined effects are consistent with TRN-driven hyperpolarization of this neuron and a shift to burst mode.

To test the impact of eGLuc-VChR1 on bursting in these targets, we will use a miniaturized device carrying 64 electrodes (16 drives) simultaneously at <2 grams can be used, with sustained recording quality for up to 1 year in mice. Chronic multielectrode recording provides an ideal method for measuring luminescent protein/light-gated ion channel impact on burst probability. In a recent analysis, the number of well-isolated single units recorded across 5 mice, 16 tetrodes/mouse in neocortex, TRN and VP was mean=25.8 units/day N=75 recording days. High numbers of simultaneous neural recordings increase not only our rate of observation, but also the ability to measure burst synchrony, a key target of modulation. This method can be used for assessing the impact of luminescent protein/light-gated ion channel control of bursting relative to behavior (e.g., regulation of seizures or promotion of sleep behavior by controlling bursting). For example, mice can be affixed with a stereolithographic fabricated head post. Mice can be tested starting 1.5 weeks post-transduction surgery. The miniaturized device can be integrated with fiber optics that can be freely controlled in depth. These fibers can be used to drive local neurons to determine if they express the luminescent proteins and light-gated ion channels. Photon production activity can be recorded through these fibers using methods known in the art to track the time course of bioluminescence activation by CTZ.

Figure 13:
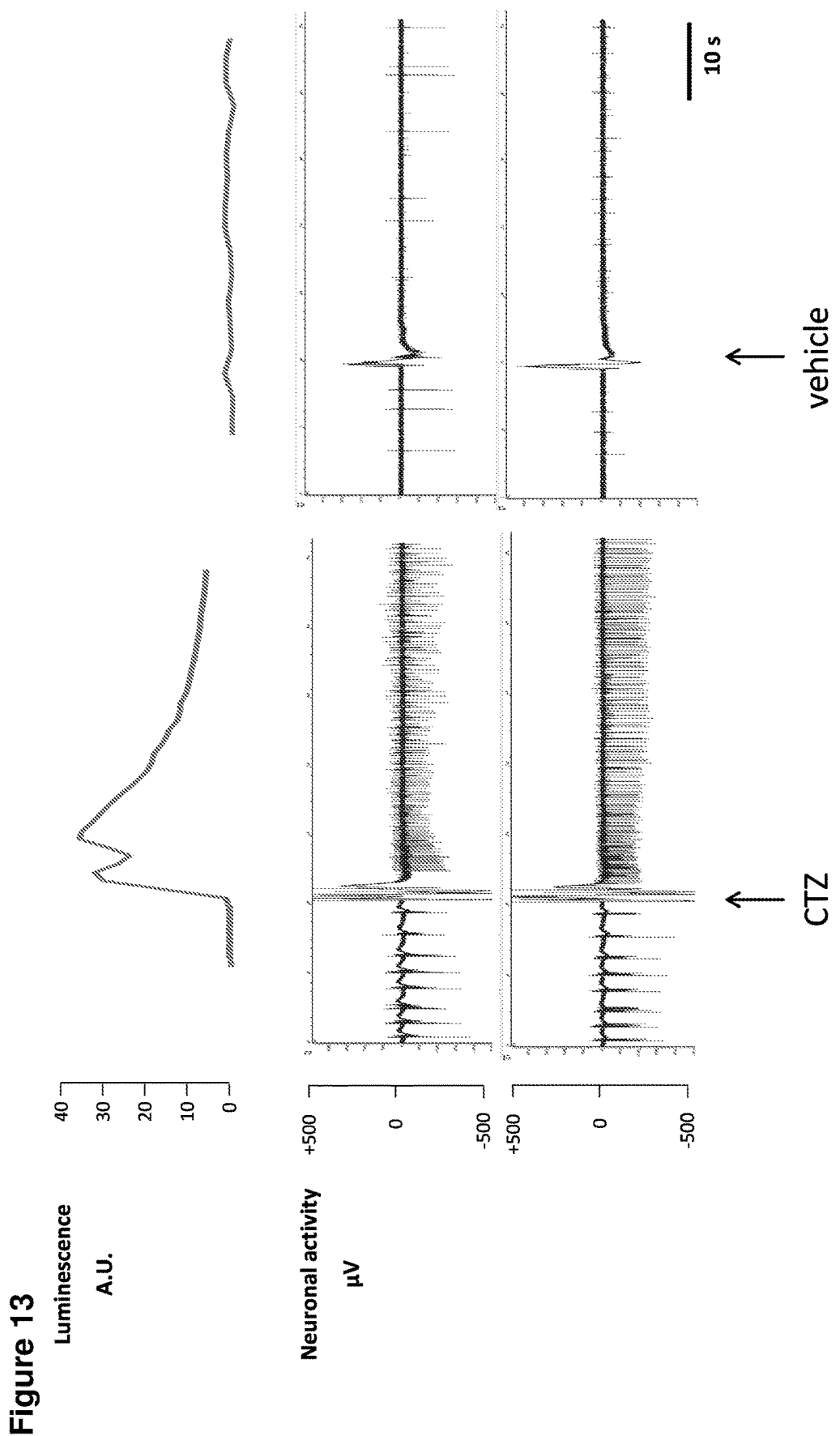
FIG. 13 is a series of graphs showing the luminescence and neuronal activity of rat cortical neurons in response to contacting with coelenterazine (CTZ) or with the vehicle. As can be seen from the graphs, contacting the neurons with CTZ results in luminescence, whereas no luminescence above noise is observed after the neurons are contacted with the vehicle.

Excitable cells (rat cortical neurons) expressing a light-gated ion channel (VChR1) fused to a luminescent protein (*Gaussia* luciferase) were cultured on multi electrode arrays (MEA), as shown in FIGS. 12A-12D. The results are shown in FIG. 13 Under continuous recording MEA dishes were injected (see arrows) with CTZ or with vehicle. Upon injection a pronounced artifact was observed (see FIG. 13). This was followed by desynchronized spiking with bioluminescence: the rhythmic spiking before light induction by CTZ is replaced by non-synchronized spiking. In contrast, vehicle injection causes the artifact, but neuronal spiking pattern is not altered. This example shows desynchronization at the level of a population of neurons. A given population in a MEA culture dish shows a specific firing pattern (see FIG. 13; for each of the two cultures—each example is from a different electrode on the MEA). Neurons in the culture express LMO3 (luminopsins 3, a fusion of sbGLuc and VChR1). Upon application of substrate (CTZ), but not of vehicle, the luciferase emits light which activates the channelrhodopsin, resulting in changed spiking activity (see before and after CTZ). This is a fairly good simulation of how an area in the brain which is firing in a certain, detrimental pattern can be de-coupled from this pattern and be pushed into a new firing pattern.

Other luminescent proteins/light-gated ion channels can be expressed in mice by injecting them stereotaxically with small volumes of virus-containing solutions. After about 1.5 weeks, brain slices can be prepared for in vitro recordings. Reporter expression can be mapped onto the nuclear anatomy as defined under DIC optics. Whole-cell recordings can be made in current-clamp from relay or TRN neurons, using specific antagonists to block AMPA, NMDA, GABAA, and GABAB synaptic receptors. Selective thalamic transduction of TRN cells can be achieved using the AAV2/9-hSyn virus, and of VPm using an AAV with floxed constructs injected into the Nsmf-Cre line (a GENSAT mouse line selective for VPm/VPI thalamic nuclei).

Figure 8:
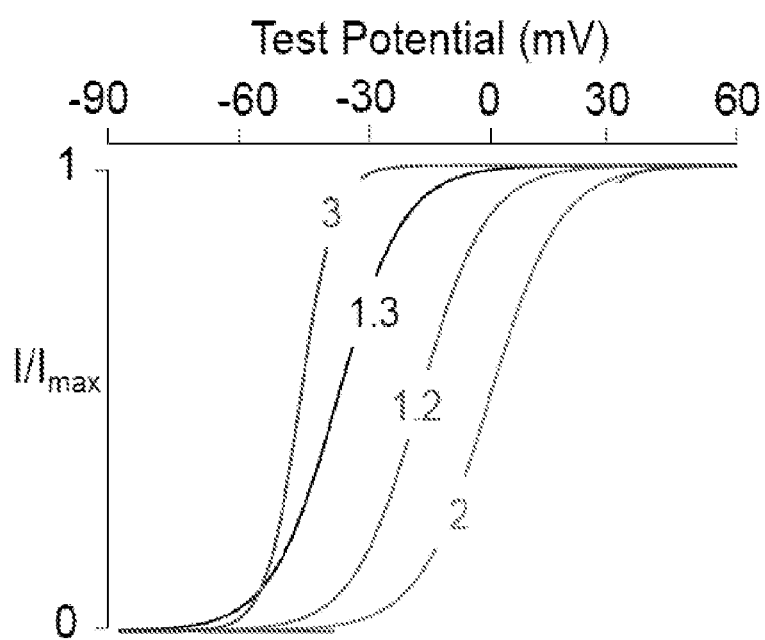
FIG. 8 is a graph showing activation curves for Cav channels. The graph shows that the combination of Cav1, Cav2, and Cav3 channels supports $Ca^{2+}$ entry between membrane voltages from −70 mV to +50 mV.
Figure 9A:
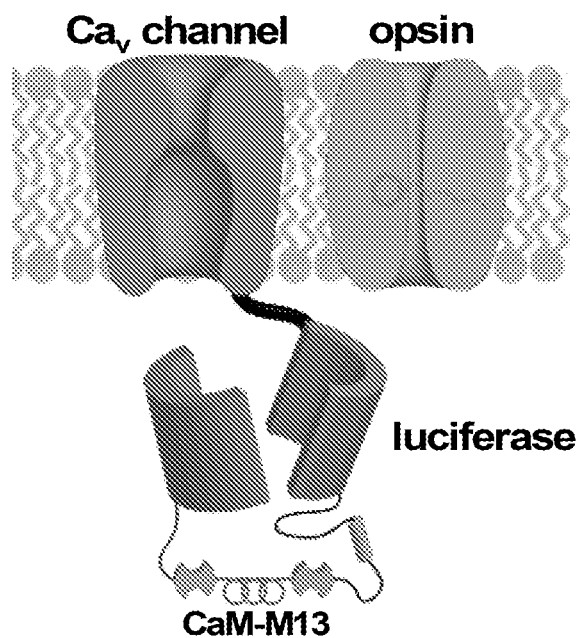
FIG. 9A is a scheme showing the voltage-gated calcium ion channel (Cav) tethered to a luminescent protein that contains a calcium-binding motif called split luminescent protein. The Cav channel is positioned in close proximity to the light gated ion channel.
Figure 9B:
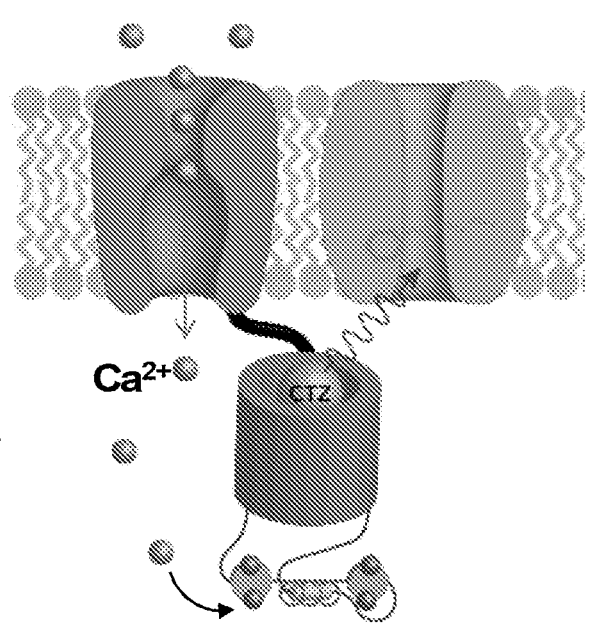
FIG. 9B is a scheme showing the entry of $Ca^{2+}$ ions into the cell through an open pore in the Cav channel. The opening of the pore depends on the intrinsic voltage-sensitivity of the specific Cav channel. $Ca^{2+}$ ions reconstitute the split luciferase, which, in the presence of coelenterazine (CTZ), emits light that opens the adjacent light-gated ion channel.
Figure 10:
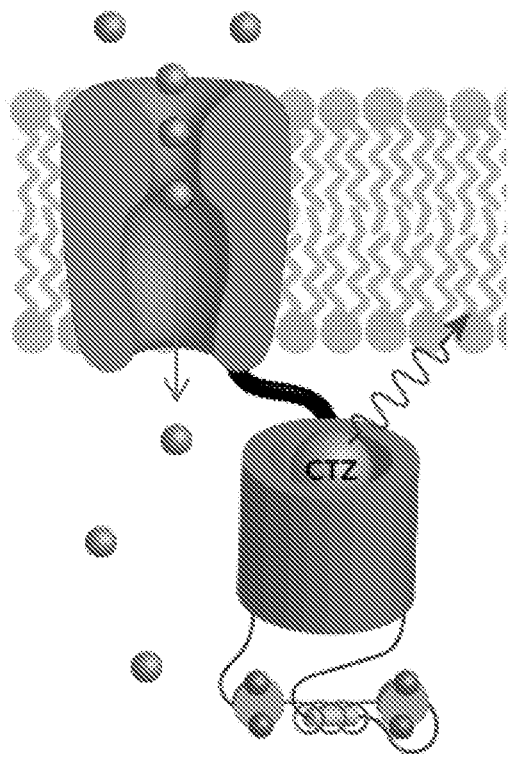
FIG. 10 is a scheme showing the different chimeric configurations that link Cav channel, Ca2+ sensing luminescent protein, and light gated ion channel.
Figure 11:
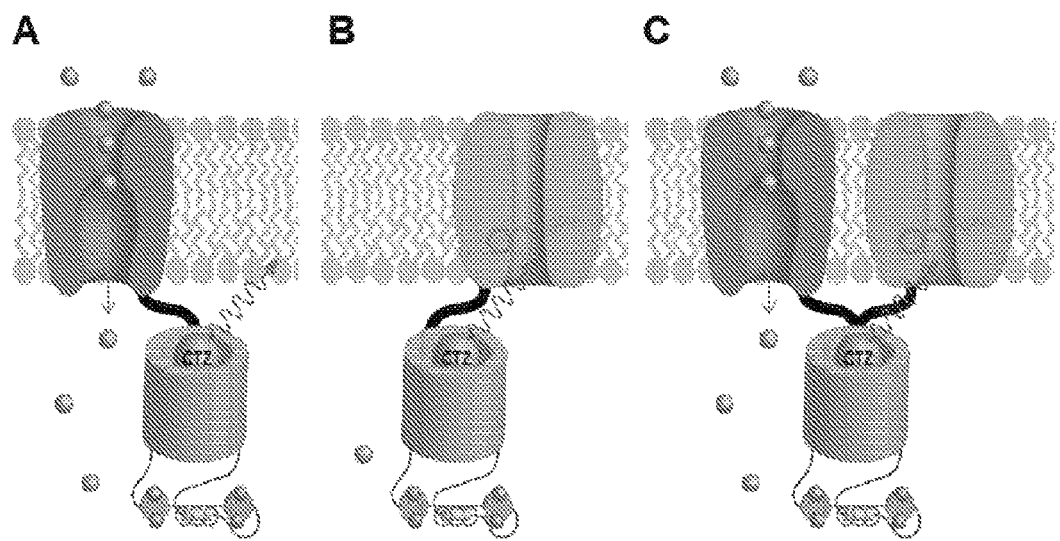
FIG. 11A is a scheme showing that a split luminescent protein and a Cav channel can be used and a trafficking motif can be fused to the light gated ion channel (not shown in A but shown in B) to bring it close to the split luminescent protein and Cav channel construct.
FIG. 11B is a scheme showing that the luminescent protein can be tethered to the light gated ion channel, and this construct would have motifs to target it close to the Cav channel.
FIG. 11C is a scheme showing a configuration of a fusion protein combining the voltage-gated ion channel, split luminescent protein, and the light gated ion channel.
Figure 12A:
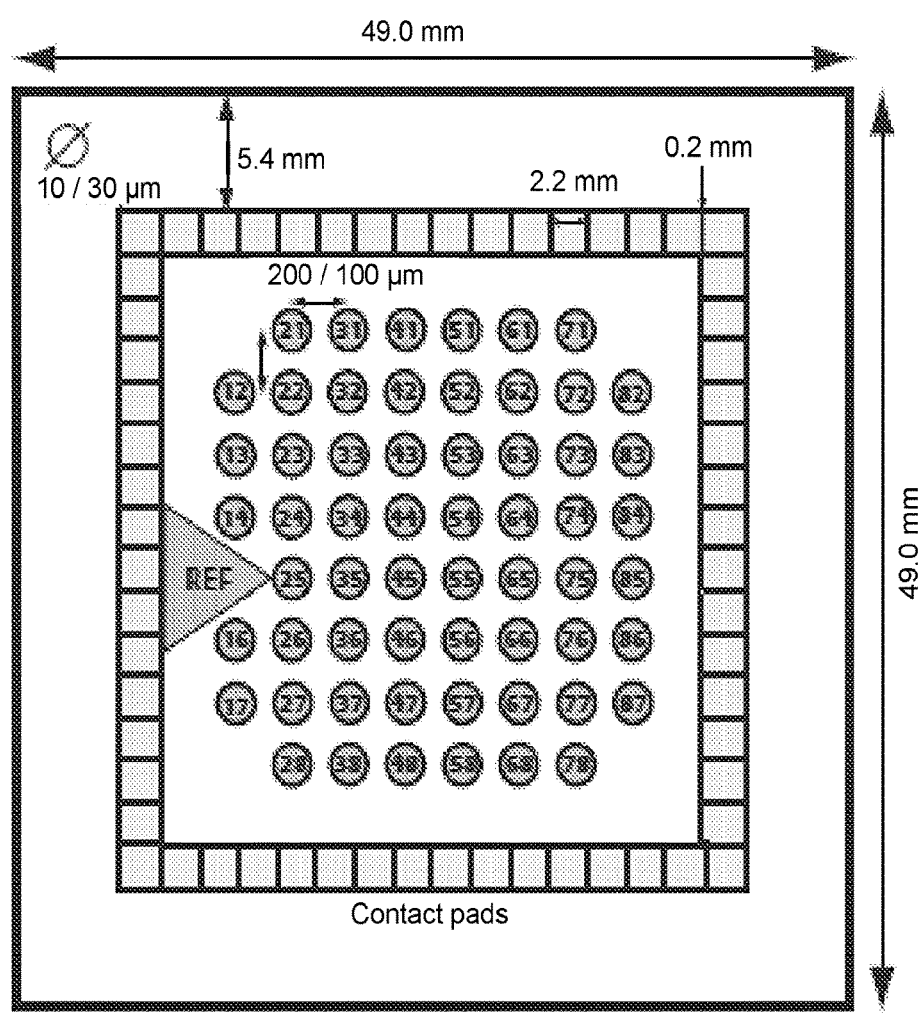
FIGS. 12A-12D show multi electrode arrays used in the in vitro experiments on rat cortical neurons.
Figure 12B:
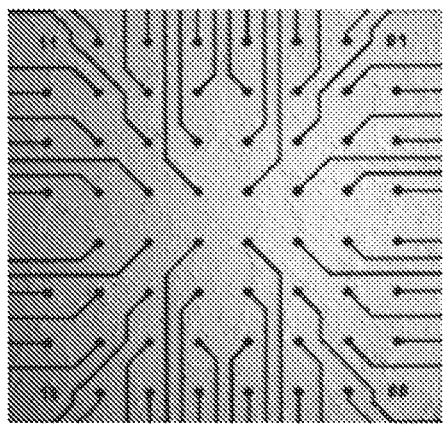
Figure 12C:
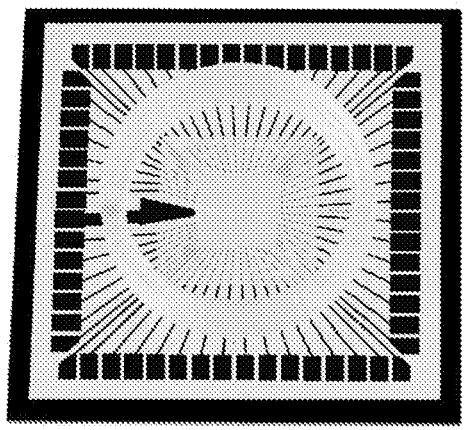
Figure 12D:
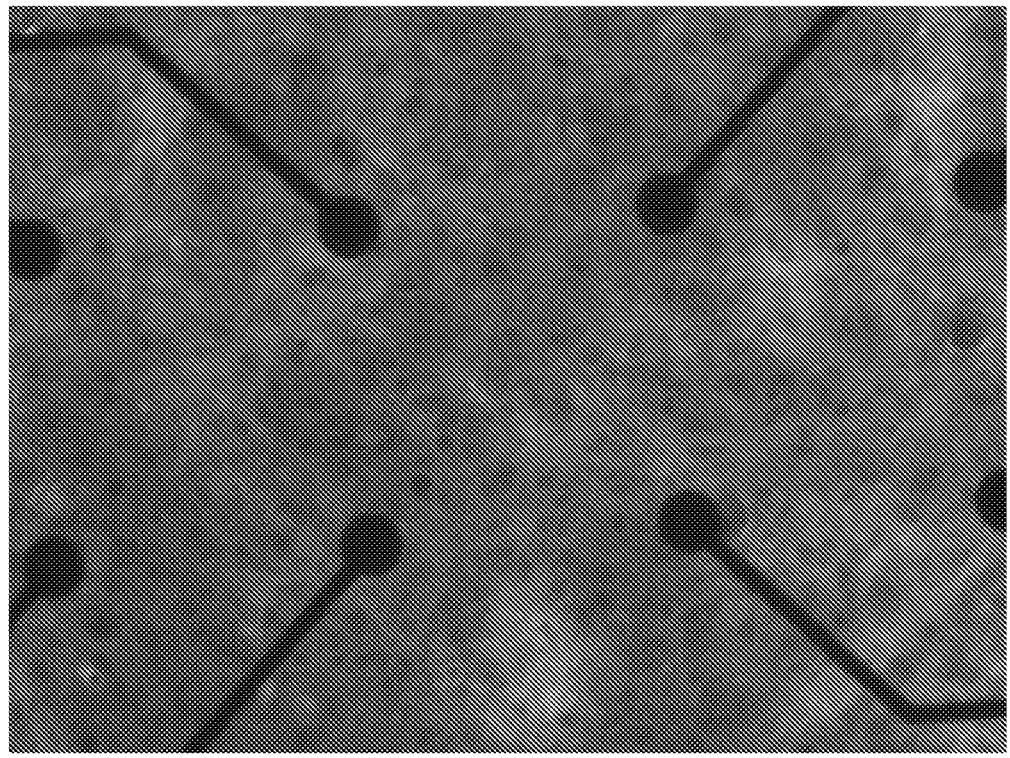

Persistently active luminescent protein/light gated ion channel fusion proteins can be tested for their control of the activity of an excitable cell. The eGluc-VChR1 data thus far obtained have shown efficacy in regulating features of burst expression in vitro and in vivo (FIGS. 5 and 8). As indicated in FIG. 8, the strong depolarization generated by this modulator in vivo in the TRN may be an effective method for increasing burst activation in VP relay neurons. As such, the net effect of strong local TRN drive with eGluc-VChR1 may be increased VP bursting. In contrast, the more subtle membrane potential manipulations desired for altering bursting while minimally impacting overall rate may be served by the weaker bioluminescence/optogenetic reactions generated by GLuc-ChR2, which employs non-enhanced *Gaussia* as its bioluminescent driver. Other fusion proteins including a luminescent protein and a light-gated ion channel (luminopsins) can be tested, e.g., LumiStepOpsins-1 and -2. In these variants, enhanced GLuc (eGLuc) was tethered to the D156A and C128S variants of ChR2, leading them to be switched "on" and demonstrate sustained depolarization with transient light pulses. These variants may enhance the duration of burst modulation achieved by a single luciferin presentation. Other luminopsins that can be tested include those in which non-enhanced and enhanced *Gaussia* are tethered to light-gated ion channels, such as NpHR, ArchT, and Mac to hyperpolarize modestly and promote burst mode and burst probability.

Luminescent proteins can be activated by superfusion of a luciferin, e.g., CTZ (10-200 µM). As CTZ is applied, neuronal bursting properties and emitted light can be recorded. Neural bursting properties can be tested continually before, during, and after CTZ application. Typically two or more TRN or VPm neurons are recorded simultaneously to maximize yield. Standardized protocols will be used to test for bursting probability and characteristics. First, 2 second hyperpolarizing current pre-pulses can be used to step the membrane potential between −110 mV and rest in increments of −10 mV (current pulse steps are predefined by each cell's input resistance). Rebound bursts and their probability, latency, and spiking properties can be measured at the end of each current pulse. Second, it is possible to use a ramp current stimulus protocol that drives membrane potential from a hyperpolarized level (−90 mV) where T channels are inactivated, through a voltage range that assays, initially, bursting and subsequently tonic spiking domains (current pulses of 300-500 pA, durations of 2-8 seconds). The effect of CTZ on membrane potential and bursting can be compared with similar tests of the efficacy of direct light activation of OG elements on potential and bursting.

Transduction of TRN cells can be achieved using the AAV2/9-hSyn virus to drive expression of LMOs (initially eGLuc-VChR1). Thalamic slices can be maintained in vitro, and whole-cell recordings can be obtained simultaneously from anatomically aligned TRN neurons and VPm relay cells. Bath applications of high concentrations of CTZ are expected to depolarize TRN cells and induce tonic firing due to sustained depolarization. Recordings in VPm cells may reveal tonic IPSPs and sustained hyperpolarization due to TRN-mediated GABAergic inhibition. Using antagonists of GABAA and GABAB receptors, their contributions to this inhibition can be tested. The effects of CTZ application (without GABA antagonists) on VPm bursting can be tested too.

Example 4: Modulating Activity of an Excitable Cell by Expressing a Luminescent Protein and a Light-Gated Ion Channel in Different Cells The ability of luminescent protein-expressing cells to regulate local light-gated ion channels containing axonal synaptic inputs. Bioluminescenece constructs can be expressed in VPm relay neurons. Relay cells are primarily regulated by three sets of extrinsic inputs: those from the TRN as discussed above, those from descending neocortical axons (corticothalamic pathways), and those carrying neuromodulators (e.g. acetylcholine). By hyperpolarizing, depolarizing, or regulating voltage-dependent conductances, each type of input can radically alter relay burst probability. Acetylcholine, for example, acts through multiple mechanisms that have strong but complex effects to suppress or enhance thalamic bursting.

Light-gated ion channel activation in one cell by a bioluminescence from another cell can overcome a shortcoming of other, more global, methods of activating these three sources of input described above. Each set of inputs has multiple targets beyond the local thalamic neurons, as neuromodulatory systems project throughout the brain, and corticothalamic and TRN axons spread widely through the thalamus. Stimulating these inputs directly, for example by fiber optic placement in the originating nuclei, can therefore have a widespread impact. The approach described in this example can restrict regulation to the set of inputs adjacent to cells expressing a luminescent protein.

There are three approaches that can be used to express a light-gated ion channel: ChAT-ChR2 transgenic mice expressing ChR2 in ACh axons to thalamus; transduction with AAV2/9 as described above to transduce VChR1 in TRN (FIG. 5A); or use Ntsr1-Cre line to express VChR1 selectively in corticothalamic terminals. A luminescent protein can be expressed in proximal cells. For example, enhanced *Gaussia* luciferase (the luciferase in eGLuc-VChR1 used in the Examples above) can be expressed selectively in TRN or relay neurons, as described in Example 4. CTZ can be infused to activate the luciferase while measuring: 1) postsynaptic responses from each pathway (membrane potential, input resistance, synaptic potentials), 2) tests of selective antagonists to determine whether the transmitter selectivity for each input pathway meets expectations (e.g., muscarinic or nicotinic inputs from ACh pathways), and 3) burst characteristics of the TRN or relay cells using testing procedures described in Example 3. The measurements can be done in thalamic slices with recording from TRN or relay neurons.

Example 5: Selective Modulation of the Activity of an Excitable Cell with Conjugates Containing a Luminescent Protein and a Light-Gated Ion Channel In this example, constructs containing a $Ca^{2+}$-sensitive luminescent protein are prepared and tested. Specifically, blue light-sensing activating (VChR1) and silencing (Mac) light-gated ion channels can be combined with aequorin (AEQ) and the AEQ-fluorophore fusion protein, GFP-AEQ. Likewise, red-shifted light-gated ion channels (e.g., ReaChR and Halo) can be combined with appropriate fluorescent proteins (e.g., tdTomato) or produce tdTomato-AEQ (tdT-AEQ) construct. Bioluminescent resonant energy transfer from the luciferase to the fluorescent protein has been shown to enhance photon production, and allows tuning of the wavelength of emission.

Constructs can be as follows: (light-gated ion channel)-linker-Aequorin and (light-gated ion channel)-fluorophore-linker-Aequorin. The mammalian expression vector pcDNA3.1 under control of the CAG promoter can be used. The fluorophore can be a fluorescent protein (e.g., GFP). The linker can be $(SGGSGSGGQ)_5SGLRS$ (SEQ ID NO: 4). Linker-Aequorin sequence and GFP-linker-Aequorin sequence can be same as those in plasmid GFP-apoAequorin, GA5v1. Aequorin can also be fused to tdTA by replacing GFP in the above plasmid with tdTomato, keeping all other sequence parts the same. Cloning can be carried out using a combination of *E. coli* recombineering, gene synthesis, and traditional ligation cloning. The constructs can be confirmed by sequencing.

Bioluminescence of the constructs can be tested as described herein and using methods known in the art. Lack of interference of aequorin (AEQ) fusion to light-gated ion channels, directly or via a fluorescent protein, with Ca2+-dependent light emission can be confirmed as follows. Each construct can be transfected into HEK293 cells by lipofection. Constructs can be co-transfected with a firefly luciferase construct (pCMV-Fluc) as internal control of transfection efficiency; Aequorin and Fluc utilize different substrates (CTZ and D-luciferin, respectively) and can thus be interrogated independently. Transfected cells can be plated in light impermeable 96 well plates and analyzed, in quadruplicates, in a luminometer, using the following variables: DNA (none, AEQ, fluorophore-AEQ, (light-gated ion channel)-AEQ, (light-gated ion channel)-fluorophore-AEQ), $Ca^{2+}$ (none, 0.1 mM, 1 mM, 10 mM final concentration); substrate (none, CTZ to 3 µM final concentration), $Ca^{2+}$ ionophore (none, ionomycin to 2 µM final concentration). Luminescence is expected in the presence of substrate, $Ca^{2+}$, and ionophore for both AEQ alone and the AEQ-(light-gated ion channel) fusion protein. Further, luminescence intensity is expected to be highly similar, and should vary with $Ca^{2+}$ concentration.

Expression of constructs can be tested using methods known in the art and those described herein. Constructs carrying a fluorescent protein can be transfected into both HEK cells and primary neurons plated on glass cover slips. Fluorescence microscopy can be used to test expression and subcellular distribution in neurons.

Fusion constructs described in this example can be analyzed in the human embryonic kidney cell line (tsA201). The fusion protein can be driven directly with standard light pulses to confirm the function of the light-gated ion channel. These data can be compared to tsA201 cells transfected with the relevant light-gated ion channel alone. The function of the light-gated ion channel is expected to be unaffected by conjugation to a luminescent protein as described herein. Amplitude, saturation, and time constant of inward or outward currents (voltage-clamp) and membrane depolarizations and hyperpolarizations (current clamp) generated by bioluminescence can be determined. The luminometer experiments described above can provide the range of $Ca^{2+}$ influx required to generate the highest intensity of bioluminescence. Ionomycin application can trigger inward or outward currents (voltage-clamp) and membrane depolarization or hyperpolarization (current clamp) in tsA201 cells expressing fusion proteins, but not in control cells that express either AEQ or light-gated ion channels alone. Concomitant with measuring changes in membrane conductance, light emission can be measured by luminometer (e.g., FIG. 7).

Example 6: Modulation of the Activity of an Excitable Cell by Targeting a Luminescent Protein to the Dendritic Postsynaptic Density Voltage-gated $Ca^{2+}$ channels convert membrane electrical activity into local transient changes in intracellular $Ca^{2+}$. The gating of Cav channels is sensitive to change in the membrane potential and different Cav subtypes activate over unique voltage ranges that are optimal for cellular signaling needs. The combination of Cav1, Cav2, and Cav3 channels support $Ca^{2+}$ entry between membrane voltages from −70 mV to +50 mV (FIG. 8). For example, Cav3.3, Cav2.1, Cav1.3, or Cav1.2 channels can be targeted. These channels have complementary voltage dependence and trafficking to distinct membrane regions in neurons (e.g., Cav3.3: soma; Cav2.1:presynaptic terminals; and Cav1.2:postsynaptic dendrites and soma; respectively).

In this example, two approaches are provided for bringing a luminescent protein (e.g., a $Ca^{2+}$-sensitive luminescent protein (e.g., AEQ)) to the point of voltage-dependent $Ca^{2+}$ entry into neurons. In one approach, a fusion protein Cav- (luminescent protein) can be prepared (luminescent protein can be AEQ). In Cav-AEQ, AEQ can be placed in the immediate vicinity of the inner mouth of the $Ca^{2+}$ ion pore. In another approach, a luminescent protein (e.g., a $Ca^{2+}$-sensitive luminescent protein (e.g., AEQ)) can be conjugated to a short dendritic targeting motif, which can be conjugated to either N- or C-terminus of AEQ without impacting luminescent properties of AEQ. The short dendritic targeting motif can be, e.g., ESDV, which is essential for synaptic targeting of the NMDA receptor of GluN2B subunit through high affinity binding to PSD-95, or a 12 amino acid motif, which is essential for synaptic targeting of PSD-95 to dendrites. AEQ can be a wild-type AEQ or a mutant AEQ (e.g., AEQ-D119A or AEQ-D119/A/N28L). AEQ-D119A exhibit lower $Ca^{2+}$ affinity than wild-type AEQ, thereby extending the range of responsiveness to 100 µM $Ca^{2+}$. AEQ-D119A/N28L extends the responsiveness further into mM range. In the constructs described herein, a short peptide linker (e.g., a linker having from 4 to 50 amino acids) can be used to connect a luminescent protein (e.g., AEQ) to a Cav or a targeting moiety.

First Approach.

The constructs containing Cav described above can be introduced into cells (e.g., tsA201), and CTZ-caused luminescence can be measured with a luminometer at high or low extracellular $K^+$ concentrations with varying $Ca^{2+}$ concentrations. The $Ca^{2+}$ ionophore A23187 can be added to obtain the maximum possible signal normalization. The ability of the constructs containing Cav to drive light-gated ion channels can be assessed as follows. VChR1 or Mac can be coexpressed a given construct containing Cav in tsA201 cells together with necessary auxiliary subunits required for efficient plasma membrane trafficking of Cav channels. Whole-cell recording in current clamp mode and brief 2 msec current steps can be used to initiate voltage-dependent $Ca^{2+}$ entry through the Cav channels to initiate AEQ luminescence and subsequent depolarization (VChR1) or hyperpolarization (Mac). Direct light pulses can be used to calibrate activation of VChR1 and Mac. Nanodomain proximity of AEQ to the CaV channel pore in Cav-AEQ can improve the magnitude and temporal features of ensuing luminescence. Voltage-dependent properties of Cav-AEQ can be varied through the use of different Cav channels and AEQ proteins. For example, Cav3.3-AEQ can generate luminescence at negative membrane potentials −60 mV to −30 mV, while Cav2.1-AEQ(D119A/N28L) can require prolonged and stronger membrane depolarizations at −30 mV to +30 mV.

Second Approach.

One of two dendritic localization motifs "ESDV" from GluN2B that binds PSD-95 or "IYHKVKRVIEDL" from PSD-95 can be attached to a luminescent protein for synaptic dendritic targeting. These dendritic targeting motifs can be fused to the N-terminus of a wild-type or mutant $Ca^{2+}$-sensitive luminescent protein (e.g., AEQ). For bioluminescence/optogenetic experiments, tsA201 cells can be used. Unconjugated Cav channels can be co-expressed to provide an effective source of voltage-dependent $Ca^{2+}$ entry and to compare $Ca^{2+}$-dependent luminescence of native luminescent protein (e.g., AEQ) to a construct having the luminescent protein fused to a targeting moiety. Extracellular $K^+$ can be used to achieve global changes in the membrane potential of tsA201 cells in culture and to trigger global voltage-dependent $Ca^{2+}$ entry. Ionophore A23187 can be applied at the end of the experiment to determine the maximum $Ca^{2+}$-dependent luminescence for normalization.

Example 7: $Ca^{2+}$-Sensitive Luciferase

Figure 7:
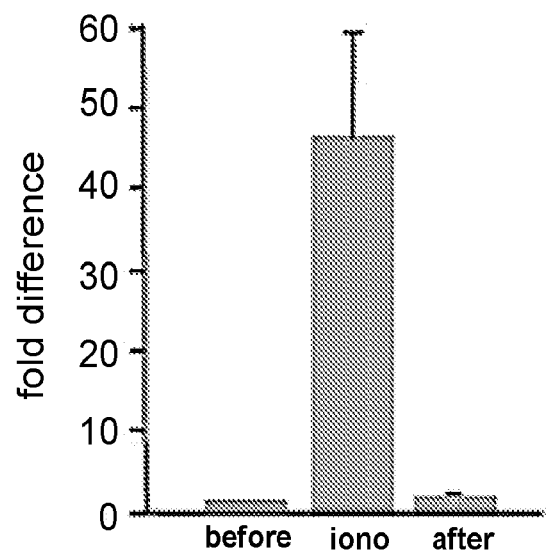
FIG. 7 is a chart showing bioluminescent $Ca^{2+}$ sensitivity of HEK cells expressing aequorin.

A luciferase (e.g., GLuc) can be modified to luminesce in a $Ca^{2+}$-sensitive manner as follows. GLuc (e.g., humanized, enhanced GLuc) can be dissected, e.g., at G93/G94 or at Q88/G89. A calmodulin domain (e.g., CAM-M13 region from Yellow Cameleon (YC.36)) can be cloned at the dissection site. The generated construct can be expressed in HEK cells. $Ca^{2+}$-dependence of luminescence of the luciferase produced in this example can be assessed as follows. HEK cells transfected with the $Ca^{2+}$-sensitive luciferase can be plated on microtiter plates and incubated with CTZ for several hours, followed by luminometer readings. Ionomycin can be injected into the wells (20 µM), and light measurements can be taken just before, immediately during, and several minutes after addition of ionomycin. Photon production can be normalized to the value before ionomycin application. This experiment was carried out with HEK cells transfected with AEQ, and the results are shown in FIG. 7. The $Ca^{2+}$-sensitive luciferase prepared in this example can be used as part of a luminescent protein in the Examples described above.

Other Embodiments

Various modifications and variations of the described compositions and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A method of desynchronizing the activity of a neuron expressing a luminescent protein and a second excitable cell located in a tissue in a mammal, wherein the location of second excitable cell is such that light from the second excitable cell is receivable by the neuron, wherein the second excitable cell expresses a conjugate of a light-gated ion channel and a subcellular element, the method comprising:
   contacting a luciferin with the neuron,
   wherein the luciferin undergoes an oxidation reaction mediated by the luminescent protein to produce light, thereby modulating the activity of the neuron.

2. The method of claim 1, wherein the subcellular element is a voltage-gated ion channel.

3. A method of desynchronizing the activities of neurons and excitable cells in a tissue in a mammal, wherein the locations in the tissue of the second excitable cells are such that light from the second excitable cells is receivable by the neurons, the method comprising:
   expressing a light-gated ion channel in a first population of excitable cells in the tissue,
   expressing a luminescent protein in a second population of neurons in the tissue, and
   contacting the tissue with a luciferin,
   wherein the luciferin reacts with the luminescent protein to produce light,
   thereby modulating the activity of the light-gated ion channel and
   thereby desynchronizing the activity of neurons and excitable cells in the tissue.

4. A method of desynchronizing the activities of neurons and excitable cells in a tissue, wherein the locations of the second excitable cell are such that light from the second excitable cells is receivable by the neurons, the method comprising:
   contacting the tissue with a luciferin,
   wherein the tissue comprises excitable cells heterogeneously expressing a light-gated ion channel and further comprises neurons expressing a luminescent protein, and
   wherein the luciferin reacts with the luminescent protein to produce light,
   thereby modulating the activity of the light-gated ion channel and
   thereby desynchronizing the activities of the neurons and the excitable cells in the tissue.

5. The method of claim 3, wherein the tissue further comprises excitable cells expressing a second luminescent protein and a second light-gated ion channel,
wherein the luciferin undergoes an oxidation reaction mediated by the second luminescent protein to produce light,
thereby modulating the activity of the second light-gated ion channel and
thereby enhancing the treating of the disease or condition.

6. The method of claim 5, wherein the excitable cells heterogeneously express the second luminescent protein and the second light-gated ion channel.

7. A method of desynchronizing the local activities of a neuron and an excitable cell in a tissue, wherein the location of second excitable cell is such that light from the second excitable cell is receivable by the neuron, the method comprising:
contacting the tissue with a luciferin, the tissue comprising:
the neuron, expressing a conjugate comprising:
a luminescent protein, and
a voltage-gated ion channel proximal to the excitable cell, and
the excitable cell expressing a light-gated ion channel,
wherein the luciferin undergoes an oxidation reaction mediated by with the luminescent protein to produce light,
thereby modulating the activity of the light-gated ion channel and
thereby desynchronizing the local activities of the neuron and the excitable cell.

8. A method of desynchronizing neurons and excitable cells in a tissue, the method comprising:
contacting the tissue with a luciferin,
wherein at least one the excitable cells is expressing a light-gated ion channel,
wherein the location of second excitable cell is such that light from the second excitable cell is receivable by the neuron, and
wherein the tissue comprises a neuron expressing a conjugate comprising
a luminescent protein and a voltage-gated ion channel,
wherein the luciferin undergoes an oxidation reaction mediated by the luminescent protein to produce light,
thereby modulating the activity of the light-gated ion channel, and
thereby desynchronizing activity of the neurons and excitable cells.

9. The method of claim 8, wherein the voltage-gated ion channel is a Cav channel.

10. The method of claim 9, wherein the Cav channel is Cav1.2, Cav2.1, or Cav3.3.

11. The method of claim 3, wherein luminescence of the luminescent protein is dependent on concentration of $Ca^{2+}$ ions.

12. The method of claim 3, wherein the luminescent protein comprises a luciferase or a photoprotein.

13. The method of claim 12, wherein the luminescent protein is a luciferase that is a *Gaussia* luciferase or the photoprotein that is Aequorin.

14. The method of claim 3, wherein the luminescent protein comprises
a fluorescent protein; or
wherein the luminescent protein comprises a calmodulin domain or a $Ca^{2+}$-binding domain thereof.

15. The method of claim 14, wherein the luminescent protein comprises the fluorescent protein that is a Green Fluorescent Protein, a Red Fluorescent Protein, or a Yellow Fluorescent Protein.

16. The method of claim 3, wherein the light-gated ion channel is ChR1, ChR2, VChR1, ChR2 C128A, ChR2 C128S, ChR2 C128T, ReaChR, C1V1, iC1C2, ChD, ChEF, ChF, ChIEF, NpHR, eNpHR, Halo, Arch 3.0, Arch T 3.0, Mac 3.0, or melanopsin, or a chimera of these proteins or a natural or an engineered variant thereof.

17. The method of claim 3, wherein the luciferin is a coelenterazine.

18. The method of claim 3, wherein the excitable cell is an endocrine cell that is a pituitary cell, a β-cell in an islet of Langerhans, or an adrenal medullar cell.

19. The method of claim 3, wherein the tissue is subthalamic nucleus or thalamic reticular nucleus.

20. The method of claim 3, wherein the step of contacting the luciferin comprises expressing the luciferin in a cell in the tissue.

* * * * *